United States Patent
Stadtmueller et al.

(10) Patent No.: US 7,241,769 B2
(45) Date of Patent: Jul. 10, 2007

(54) PYRIMIDINES AS PLK INHIBITORS

(75) Inventors: Heinz Stadtmueller, Gaweinstal (AT);
Harald Engelhardt, Ebreichsdorf (AT);
Ulrich Reiser, Vienna (AT); Stephan Karl Zahn, Vienna (AT); Rudolf Hauptmann, Ebreichsdorf (AT);
Martin Steegmaier, Vienna (AT);
Ulrich Guertler, Vienna (AT);
Matthias Hoffmann, Mittelbiberach (DE); Matthias Grauert, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 11/132,091

(22) Filed: May 18, 2005

(65) Prior Publication Data
US 2005/0261295 A1 Nov. 24, 2005

(30) Foreign Application Priority Data
May 19, 2004 (EP) .................................. 04011911

(51) Int. Cl.
C07D 239/42 (2006.01)
C07D 239/46 (2006.01)
A61K 31/505 (2006.01)
A61P 35/00 (2006.01)

(52) U.S. Cl. .................. 514/275; 544/323; 544/324
(58) Field of Classification Search ............... 544/323, 544/324; 514/275
See application file for complete search history.

(56) References Cited
U.S. PATENT DOCUMENTS
6,593,326 B1 7/2003 Bradbury et al.
2003/0114472 A1 6/2003 De Corte et al.
2004/0039005 A1 2/2004 De Corte et al.
2005/0090493 A1 4/2005 Breault et al.

FOREIGN PATENT DOCUMENTS
WO  WO 2000/12485    3/2000
WO  WO 2000/27825    5/2000
WO  WO 2004/080980   9/2004
WO  WO 2004080980 A1 * 9/2004

OTHER PUBLICATIONS

Cecil Textbook of Medicine, edited by Bennet, J.C., and Plum F., 20th edition, vol. 1, 1004-1010. 1996.*
Ahmed FASEB Journal 18, 5-7, 2004.*
Turner et al., Current Pharmaceutical Design. 2, 209-224, 1996.*
Sugar et al., Diagn. Microbiol. Infect. Dis. 21: 129-133, 1995.*
Snyder et al., J. Med. Liban 48(4): 208-214, 2000.*

* cited by examiner

Primary Examiner—Venkataraman Balasubramanian
(74) Attorney, Agent, or Firm—Michael P. Morris; Philip I. Datlow; Mary-Ellen M. Devlin

(57) ABSTRACT

The present invention comprises compounds of general formula (1)

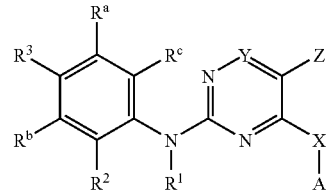

wherein
A, X, Y, Z, $R^a$, $R^b$, $R^c$, $R^1$, $R^2$ and $R^3$ are defined as in claim 1, which are suitable for the treatment of diseases characterised by excessive or anomalous cell proliferation, and the use thereof for preparing a pharmaceutical composition with the above-mentioned properties.

13 Claims, No Drawings

PYRIMIDINES AS PLK INHIBITORS

The present invention relates to new pyrimidines of general formula (1)

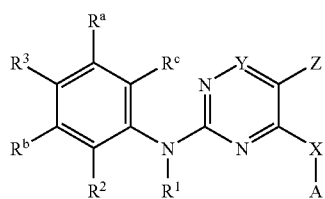

wherein the groups A, X, Y, Z, $R^a$, $R^b$, $R^c$, $R^1$, $R^2$ and $R^3$ have the meanings given in the claims and specification, the isomers thereof, processes for preparing these pyrimidines and their use as pharmaceutical compositions.

BACKGROUND TO THE INVENTION

Tumour cells wholly or partly elude regulation and control by the body and are characterised by uncontrolled growth. This is due on the one hand to the loss of control proteins such as for example Rb, p16, p21 and p53 and also to the activation of so-called accelerators of the cell cycle, the cyclin-dependent kinases.

Studies in model organisms such as *Schizosaccharomyces pombe, Drosophila melanogaster* or *Xenopus* as well as investigations in human cells have shown that the transition from the G2 phase to mitosis is regulated by the CDK1/cyclin B kinase (Nurse, 1990). This kinase, which is also known as "mitosis promoting factor" (MPF), phosphorylates and regulates a plurality of proteins, such as e.g. nuclear lamina, kinesin-like motor proteins, condensins and Golgi Matrix Proteins, which play an important part in the breakdown of the nuclear coat, in centrosome separation, the structure of the mitotic spindle apparatus, chromosome condensation and breakdown of the Golgi apparatus (Nigg, 2001). A murine cell line with a temperature-sensitive CDK-1 kinase mutant shows a rapid breakdown in CDK-1 kinase after temperature increase and a subsequent arrest in the G2/M phase (Th'ng et al., 1990). The treatment of human tumour cells with inhibitors against CDK1/cyclin B, such as e.g. butyrolactone, leads to an arrest in the G2/M phase and subsequent apoptosis (Nishio, et al. 1996).

Moreover, the protein kinase Aurora B has also been described as having an essential function during entry into mitosis. Aurora B phosphorylates histone H3 on Ser10 and thereby initiates chromosome condensation (Hsu, J. Y. et al., 2000). A specific cell cycle arrest in the G2/M phase may, however, also be initiated e.g. by inhibition of specific phosphatases such as e.g. Cdc25C (Russell and Nurse, 1986). Yeasts with a defective Cdc25 gene arrest in the G2 phase, whereas overexpression of Cdc25 leads to premature entry into the mitosis phase (Russell and Nurse, 1987). Moreover, an arrest in the G2/M phase may also be initiated by inhibition of specific motor proteins, the so-called kinesins such as for example Eg5 (Mayer et al., 1999), or by microtubuli stabilising or destabilising agents (e.g. colchicin, taxol, etoposide, vinblastine, vincristine) (Schiff and Horwitz, 1980).

In addition to the cyclin-dependent and Aurora kinases the so-called polo-like kinases (PLK), a small family of serine/threonine kinases, also play an important role in the regulation of the eukaryotic cell cycle. PLK-1 in particular has been found to play a central role in the regulation of the mitosis phase. PLK-1 is responsible for the maturation of the centrosomes, for the activation of phosphatase Cdc25C, as well as for the activation of the Anaphase Promoting Complex (Glover et al., 1998, Qian, et al., 2001). The injection of PLK-1 antibodies leads to a G2 arrest in untransformed cells, whereas tumour cells arrest during the mitosis phase (Lane and Nigg, 1996). Overexpression of PLK-1 has been demonstrated in various types of tumour, such as non-small-cell carcinoma of the lung, plate epithelial carcinoma, breast and colorectal carcinoma. Therefore, this category of proteins also presents an interesting point of attack for therapeutic intervention in proliferative diseases (Descombes and Nigg, Embo J, 17; 1).

Pyrimidines are generally known as inhibitors of kinases. Thus, for example, pyrimidines are described as an active component with an anticancer activity in International Patent Application WO 00/53595, which describes the use of 2,4,5-substituted pyrimidines with a heterocyclic group in the 4-position and an anilino group in the 2 position, which in turn comprises a side chain with the length of at least one n-propyl group.

Moreover, International Patent Application WO 00/39101 describes the use of 2,4,5-substituted pyrimidines as compounds with an anticancer activity which are linked in the 2- and 4-position with an aromatic or heteroaromatic ring, at least one of which comprises a side chain with the length of at least one n-propyl group.

International Patent Application WO 97/19065 further proposes the use of 2,4,5-substituted pyrimidines with a 3,4-dialkoxyanilino group in position 2 as kinase inhibitors.

International Patent Application WO 02/04429 describes 2,4,5-substituted pyrimidines with a cyano group in position 5 and their cell cycle inhibiting effect.

International Patent Application WO 03/063794 describes the use of 2,4-pyrimidinediamines as inhibitors of the IgE and/or IgG receptor signal cascade.

Antiviral 2,4,5-substituted pyrimidines, wherein the groups $R^c$ and $R^d$ form a heteroaromatic five-membered ring at the nitrogen of the 4-position, are known from International Patent Application WO 99/41253.

2,4,5-substituted pyrimidines which carry (hetero)aryls in position 2 and 4 (WO00/27825) and also 2,4,5-substituted pyrimidines which carry a (hetero)aryl group functionalised with a nitrile group in position 2 or 4 (EP 0 945 443 A1) are described as having an antiviral activity.

The aim of the present invention is to indicate new active substances which may be used for the prevention and/or treatment of diseases characterised by excessive or anomalous cell proliferation.

DETAILED DESCRIPTION OF THE INVENTION

It has now been found that, surprisingly, compounds of general formula (1), wherein the groups A, X, Y, $R^a$, $R^b$, $R^c$, $R^1$, $R^2$ and $R^3$ are defined as hereinafter, act as inhibitors of specific cell cycle kinases. Thus, the compounds according to the invention may be used for example for the treatment of diseases associated with the activity of specific cell cycle kinases and characterised by excessive or anomalous cell proliferation.

The present invention relates to compounds of general formula (1)

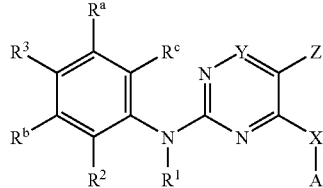

(1)

wherein
X denotes —NR$^{1a}$, O or S, and
Y denotes CH or N, and
Z denotes hydrogen, halogen, C$_{1-3}$-alkyl, C$_{2-3}$-alkenyl, C$_{2-3}$-alkynyl, halogen-C$_{1-3}$-alkyl, —COH, —C(=O)—C$_{1-3}$-alkyl, —C(=O)—C$_{2-3}$-alkenyl, —C(=O)—C$_{2-3}$-alkynyl, —C(=O)C$_{1-3}$-alkyl-halogen and pseudohalogen; and
A is selected from formulae (i) or (ii)

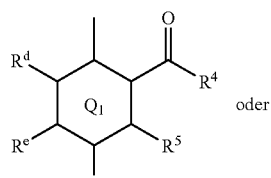

(i)

oder

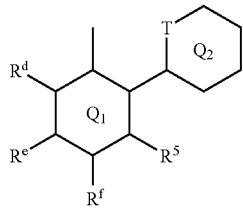

(ii)

and
Q$_1$ denotes mono- or bicyclic aryl compounds; and
Q$_2$ denotes mono- or bicyclic heteroaryl compounds; and
T denotes N, O or S, and
R$^1$ and R$^{1a}$ denotes hydrogen or methyl, and
R$^2$ denotes a group selected from among —Cl, —Br, —I, —OR$^6$, —C(=O)R$^6$, —C(=O)NR$^6$R$^7$, —NR$^6$ R$^7$, —NR$^6$C(=O)R$^7$, —NR$^6$SO$_2$R$^7$, —N=CR$^6$R$^7$, —SR$^6$, —SOR$^6$, —SO$_2$NR$^6$R$^7$ and pseudohalogen, or an optionally mono- or polysubstituted group selected from among C$_{1-6}$-alkyl, C$_{2-6}$-alkenyl, C$_{2-6}$-alkynyl, C$_{3-6}$-cycloalkyl, aryl, heterocyclyl and heteroaryl, while the substituent(s) may be identical or different and are selected from among halogen, —NO$_2$, —OR$^6$, —C(=O)R$^6$, —C(=O)OR$^6$, —C(=O)NR$^6$R$^7$, —NR$^6$R$^7$, —NR$^6$C(=O)R$^7$, —NR$^6$C(=O)OR$^7$, —NR$^6$C(=O)NR$^7$R$^8$, —NR$^6$SO$_2$R$^7$, —N=CR$^6$R$^7$, —SR$^6$, —SOR$^6$, —SO$_2$R$^6$, —SO$_2$NR$^6$R$^7$, —NR$^6$SO$_2$NR$^7$R$^8$, —OSO$_2$NR$^7$R$^8$ and pseudohalogen; and
R$^a$, R$^b$, R$^c$, R$^d$, R$^e$ and R$^f$ each independently of one another denote a group selected from among hydrogen, halogen, —NO$_2$, —OR$^6$, —C(=O)R$^6$, —C(=O)OR$^6$, —C(=O)NR$^6$R$^7$, —NR$^6$R$^7$, —NR$^6$C(=O)R$^7$, —NR$^6$C(=O)OR$^7$, —NR$^6$C(=O)NR$^7$R$^8$, —NR$^6$SO$_2$R$^7$, —N=CR$^6$R$^7$, —SR$^6$, —SOR$^6$, —SO$_2$R$^6$, —SO$_2$NR$^6$R$^7$, —NR$^6$SO$_2$NR$^7$R$^8$, —OSO$_2$NR$^7$R$^8$ and pseudohalogen; or an optionally mono- or polysubstituted group selected from among C$_{1-6}$-alkyl, C$_{2-6}$-alkenyl, C$_{2-6}$-alkynyl, C$_{3-6}$-cycloalkyl, aryl, heterocyclyl and heteroaryl, while the substituent(s) may be identical or different and are selected from among hydrogen, halogen, —NO$_2$, —OR$^6$, —C(=O)R$^6$, —C(=O)OR$^6$, —C(=O)NR$^6$R$^7$, —NR$^6$R$^7$, —NR$^6$C(=O)R$^7$, —NR$^6$C(=O)OR$^7$, —NR$^6$C(=O)NR$^7$R$^8$, —NR$^6$SO$_2$R$^7$, —N=CR$^6$R$^7$, —SR$^6$, —SOR$^6$, —SO$_2$R$^6$, —SO$_2$NR$^6$R$^7$, —NR$^6$SO$_2$NR$^7$R$^8$, —OSO$_2$NR$^7$R$^8$ and pseudohalogen; and
R$^3$ is selected from the formulae (iii)-(ix),

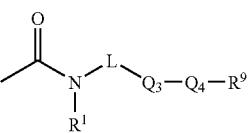

(iii)

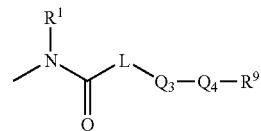

(iv)

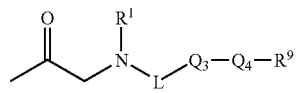

(v)

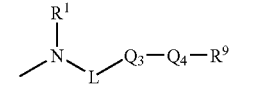

(vi)

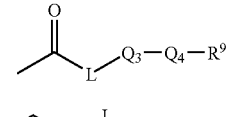

(vii)

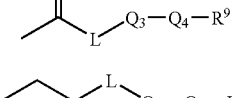

(viii)

—L—Q$_3$—Q$_4$—R$^9$ (ix)

and
R$^4$ denotes a group selected from among hydrogen, —OR$^6$, —C(=O)R$^6$, —C(=O)OR$^6$, —C(=O)NR$^6$R$^7$, —NR$^6$R$^7$, —NR$^6$C(=O)R$^7$, —NR$^6$C(=O)OR$^7$, —NR$^6$C(=O)NR$^7$R$^8$, —NR$^6$SO$_2$R$^7$, —N=CR$^6$R$^7$, —SR$^6$, —SOR$^6$, —SO$_2$R$^6$, —SO$_2$NR$^6$R$^7$, —NR$^6$SO$_2$NR$^7$R$^8$, —OSO$_2$NR$^7$R$^8$ and pseudohalogen,
or denotes a group selected from among optionally mono- or polysubstituted C$_{1-8}$-alkyl, C$_{2-10}$-alkenyl, C$_{2-10}$-alkynyl, C$_{3-8}$-cycloalkyl, aryl, heterocyclyl and heteroaryl, while the substituent(s) may be identical or different and are selected from among C$_{1-8}$-alkyl, halogen, —NO$_2$, —OR$^6$, —C(=O)R$^6$, —C(=O)OR$^6$, —C(=O)NR$^6$R$^7$, —NR$^6$R$^7$, —NR$^6$C(=O)R$^7$, —NR$^6$C(=O)OR$^7$, —NR$^6$C(=O)NR$^7$R$^8$, —NR$^6$SO$_2$R$^7$, —N=CR$^6$R$^7$, —SR$^6$, —SOR$^6$, —SO$_2$R$^6$, —SO$_2$NR$^6$R$^7$, —NR$^6$SO$_2$NR$^7$R$^8$, —OSO$_2$NR$^7$R$^8$ and pseudohalogen; and $R^5$ denotes hydrogen, halogen, —$CF_3$, $C_{1-3}$-alkyl or —$OR^6$; and $R^6$, $R^7$ and $R^8$ in each case independently of one another denote hydrogen or a group selected from among optionally mono- or polysubstituted $C_{1-5}$-alkyl, $C_{2-5}$-alkenyl, $C_{2-5}$-alkynyl, $C_{3-10}$-cycloalkyl, aryl, heterocyclyl and heteroaryl, while the substituent(s) may be identical or different and are selected from among $C_{3-10}$-cycloalkyl, aryl, heterocyclyl, heteroaryl, halogen, —$NO_2$, —$OR^{10}$, —$C(=O)R^{10}$, —$C(=O)OR^{10}$, —$C(=O)NR^{10}R^{11}$, —$NR^{10}R^{11}$, —$NR^{10}C(=O)R^{11}$, —$NR^{10}C(=O)OR^{11}$, —$NR^{10}C(=O)NR^{11}R^{12}$, —$NR^{10}C(=O)ONR^{11}R^{12}$, —$NR^{10}SO_2R^{11}$, —$N=CR^{10}R^{11}$, —$SR^{10}$, —$SOR^{10}$, —$SO_2R^{10}$, —$SO_2NR^{10}R^{11}$, —$NR^{10}SO_2NR^{11}R^{12}$, —$OSO_2NR^{10}R^{11}$ and pseudohalogen; and L denotes a bond or a group selected from among optionally mono- or polysubstituted $C_{1-16}$-alkyl, $C_{2-16}$-alkenyl, $C_{2-16}$-alkynyl, $C_{3-10}$-cycloalkyl, aryl, heterocyclyl and heteroaryl, while the substituent(s) may be identical or different and are selected from among halogen, —$NO_2$, —$OR^{10}$, —$C(=O)R^{10}$, —$C(=O)OR^{10}$, —$C(=O)NR^{10}R^{11}$, —$NR^{10}R^{11}$, —$NR^{10}COR^{11}$, —$NR^{10}C(=O)OR^{11}$, —$NR^{10}C(=O)NR^{11}R^{12}$, —$NR^{10}C(=O)ONR^{11}R^{12}$, —$NR^{10}SO_2R^{11}$, —$N=CR^{10}R^{11}$, —$SR^{10}$, —$SOR^{10}$, —$SO_2R^{10}$, —$SO_2NR^{10}R^{11}$, —$NR^{10}SO_2NR^{11}R^{12}$, —$OSO_2NR^{10}R^{11}$ and pseudohalogen; and $Q_3$ and $Q_4$ independently of one another denote a bond or a group selected from among optionally mono- or polysubstituted mono- or bicyclic heterocyclyl, while the substituent(s) may be identical or different and are selected from among methyl, ethyl, halogen, —$NH_2$, —$OH$ and pseudohalogen; and $R^9$ denotes a group selected from among optionally mono- or polysubstituted $C_{1-16}$-alkyl, $C_{2-16}$-alkenyl, $C_{2-16}$-alkynyl, $C_{3-10}$-cycloalkyl, aryl, heterocyclyl and heteroaryl, while the substituent(s) may be identical or different and are selected from among halogen, —$NO_2$, —$OR^{10}$, —$C(=O)R^{10}$, —$C(=O)OR^{10}$, —$C(=O)NR^{10}R^{11}$, —$NR^{10}R^{11}$, —$NR^{10}COR^{11}$, —$NR^{10}C(=O)OR^{11}$, —$NR^{10}C(=O)NR^{11}R^{12}$, —$NR^{10}C(=O)ONR^{11}R^{12}$, —$NR^{10}SO_2R^{11}$, —$N=CR^{10}R^{11}$, —$SR^{10}$, —$SOR^{10}$, —$SO_2R^{10}$, —$SO_2NR^{10}R^{11}$, —$NR^{10}SO_2NR^{11}R^{12}$, —$OSO_2NR^{10}R^{11}$ and pseudohalogen; and $R^{10}$, $R^{11}$ and $R^{12}$ in each case independently of one another denote hydrogen or a group selected from among optionally mono- or polysubstituted $C_{1-8}$-alkyl, $C_{2-8}$-alkenyl, $C_{2-8}$-alkynyl, $C_{3-10}$-cycloalkyl, aryl, heterocyclyl and heteroaryl, while the substituent(s) may be identical or different and are selected from among halogen, —$NH_2$, —$OH$ and pseudohalogen;

optionally in the form of the tautomers, the racemates, the enantiomers, the diastereomers and the mixtures thereof, as well as optionally the pharmacologically acceptable acid addition salts thereof.

In one aspect the invention relates to compounds of general formula (1), wherein X denotes —$NR^{1a}$ or oxygen, and A is selected from formulae (i) or (ii)

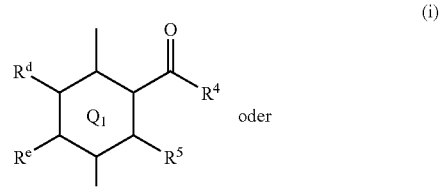

(i)

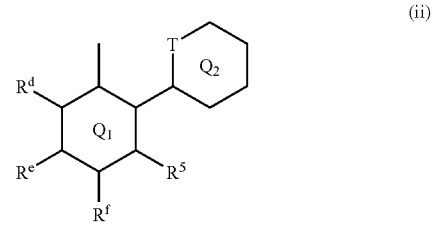

(ii)

and $Q_1$ denotes mono- or bicyclic aryl compounds; and
$Q_2$ denotes monocyclic heteroaryl compounds; and
T denotes N, O or S, and
$R^1$ denotes hydrogen; and
$R^3$ denotes formula (iii),

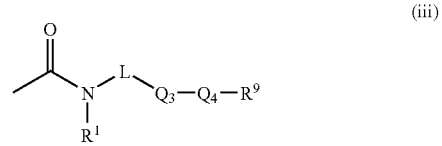

(iii)

and the other groups are as hereinbefore defined.

In another aspect the invention relates to compounds of general formula (1), wherein
Y denotes CH; and
$Q_1$ denotes monocyclic aryl compounds and the other groups are as hereinbefore defined.

In another aspect the invention relates to compounds of general formula (1), wherein
$R^c$ denotes a group selected from among hydrogen, —F, —Cl, methyl and ethyl and the other groups are as hereinbefore defined.

In another aspect the invention relates to compounds of general formula (1), wherein
$R^a$ and $R^b$ in each case independently of one another denote hydrogen or an optionally mono- or polysubstituted group selected from among $C_{1-2}$-alkyl, $C_2$-alkenyl, $C_2$-alkynyl, $C_{3-6}$-cycloalkyl, aryl, heterocyclyl and heteroaryl, while the substituent(s) may be identical or different and are selected from among hydrogen, halogen, —$NO_2$, —$OR^6$, —$C(=O)R^6$, —$C(=O)OR^6$, —$C(=O)NR^6R^7$, —$NR^6R^7$, —$NR^6C(=O)R^7$, —$NR^6C(=O)OR^7$, —$NR^6C(=O)NR^7R^8$, —$NR^6SO_2R^7$, —$N=CR^6R^7$, —$SR^6$, —$SOR^6$, —$SO_2R^6$, —$SO_2NR^6R^7$, —$NR^6$, —$SO_2NR^7R^8$, —$OSO_2NR^7R^8$ and pseudohalogen;

and the other groups are as hereinbefore defined.

In another aspect the invention also relates to compounds of general formula (1), wherein
$R^a$ and $R^b$ denote hydrogen and the other groups are as hereinbefore defined.

The invention also includes compounds of general formula (1), wherein

Z denotes halogen-$C_{1-3}$-alkyl, —COH, —C(=O)—$C_{1-3}$-alkyl, —C(=O)—$C_{2-3}$-alkenyl, —C(=O)—$C_{2-3}$-alkynyl, —C(=O)$C_{1-3}$-alkyl-halogen and pseudohalogen;

and the other groups are as hereinbefore defined.

In another aspect the invention relates to compounds of general formula (1), where Z denotes $C_{1-3}$-fluoroalkyl and
Y denotes CH and the other groups are as hereinbefore defined.

In one aspect the invention relates to compounds of general formula (1), or the pharmaceutically active salts thereof, for use as pharmaceutical compositions.

In another aspect the invention relates to compounds of general formula (1), or the pharmaceutically active salts thereof, for use as pharmaceutical compositions with an antiproliferative activity.

In an essential aspect the invention relates to compounds of general formula (1), or the pharmaceutically active salts thereof, for use as pharmaceutical compositions with an antiproliferative activity.

Moreover the invention includes compounds of general formula (1), or the pharmaceutically active salts thereof, for use as pharmaceutical compositions with an antiproliferative activity with a selective kinase-inhibiting mechanism of activity.

In one aspect the invention relates to the use of compounds of general formula (1), or the pharmaceutically active salts thereof, for preparing a pharmaceutical composition with an antiproliferative activity with a PLK inhibiting mechanism of activity.

In another aspect the invention relates to pharmaceutical preparations, containing as active substance one or more compounds of general formula (I), or the physiologically acceptable salts thereof, optionally in conjunction with conventional excipients and/or carriers.

In another aspect the invention relates to the use of one or more compounds of general formula (1) for preparing a pharmaceutical composition for the treatment and/or prevention of cancer, infections, inflammatory and autoimmune diseases.

In another aspect the invention relates to a pharmaceutical preparation containing a compound of general formula (1)

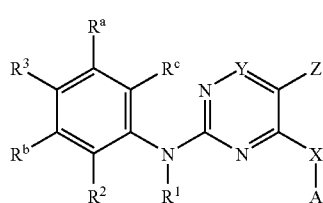

(1)

wherein
X denotes —$NR^{1a}$, O or S, and
Y denotes CH or N, and
Z denotes hydrogen, halogen, $C_{1-3}$-alkyl, $C_{2-3}$-alkenyl, $C_{2-3}$-alkynyl, halogen-$C_{1-3}$-alkyl, —COH, —C(=O)—$C_{1-3}$-alkyl, —C(=O)—$C_{2-3}$-alkenyl, —C(=O)—$C_{2-3}$-alkynyl, —C(=O)$C_{1-3}$-alkyl-halogen and pseudohalogen; and A is selected from formulae (i) or (ii)

(i)

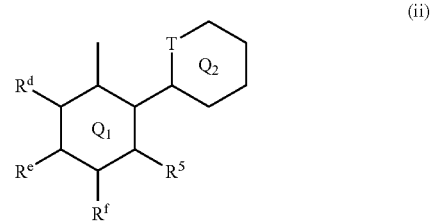

(ii)

and $Q_1$ denotes mono- or bicyclic aryl compounds; and
$Q_2$ denotes mono- or bicyclic heteroaryl compounds; and
T denotes N, O or S, and
$R^1$ and $R^{1a}$ denotes hydrogen or methyl, and
$R^2$ denotes a group selected from among —Cl, —Br, —I, —$OR^6$, —C(=O)$R^6$, —C(=O)$NR^6R^7$, —$NR^6R^7$, —$NR^6$C(=O)$R^7$, —$NR^6SO_2R^7$, —N=$CR^6R^7$, —$SR^6$, —$SOR^6$, —$SO_2R^6$, —$SO_2NR^6R^7$ and pseudohalogen, or an optionally mono- or polysubstituted group selected from among $C_{1-6}$-alkyl, $C_{2-6}$-alkenyl, $C_{2-6}$-alkynyl, $C_{3-6}$-cycloalkyl, aryl, heterocyclyl and heteroaryl, while the substituent(s) may be identical or different and are selected from among halogen, —$NO_2$, —$OR^6$, —C(=O)$R^6$, —C(=O)$OR^6$, —C(=O)$NR^6R^7$, —$NR^6R^7$, —$NR^6$C(=O)$R^7$, —$NR^6$C(=O)$OR^7$, —$NR^6$C(=O)$NR^7R^8$, —$NR^6SO_2R^7$, —N=$CR^6R^7$, —$SR^6$, —$SOR^6$, —$SO_2R^6$, —$SO_2NR^6R^7$, —$NR^6SO_2NR^7R^8$, —$OSO_2NR^7R^8$ and pseudohalogen; and $R^a$, $R^b$, $R^c$, $R^d$, $R^e$ and $R^f$ each independently of one another denote a group selected from among hydrogen, halogen, —$NO_2$, —$OR^6$, —C(=O)$R^6$, —C=O)$OR^6$, —C(=O)$NR^6R^7$, —$NR^6R^7$, —$NR^6$C(=O)$R^7$, —$NR^6$C(=O)$OR^7$, —$NR^6$C(=O)$NR^7R^8$, —$NR^6SO_2R^7$, —N=$CR^6R^7$, —$SR^6$, —$SOR^6$, —$SO_2R^6$, —$SO_2NR^6R^7$, —$NR^6SO_2NR^7R^8$, —$OSO_2NR^7R^8$ and pseudohalogen; or an optionally mono- or polysubstituted group selected from among $C_{1-6}$-alkyl, $C_{2-6}$-alkenyl, $C_{2-6}$-alkynyl, $C_{3-6}$-cycloalkyl, aryl, heterocyclyl and heteroaryl, while the substituent(s) may be identical or different and are selected from among hydrogen, halogen, —$NO_2$, —$OR^6$, —C(=O)$R^6$, —C(=O)$OR^6$, —C(=O)$NR^6R^7$, —$NR^6R^7$, —$NR^6$C(=O)$R^7$, —$NR^6$C(=O)$OR^7$, —$NR^6$C(=O)$NR^7R^8$, —$NR^6SO_2R^7$, —N=$CR^6R^7$, —$SR^6$, —$SOR^6$, —$SO_2R^6$, —$SO_2NR^6R^7$, —$NR^6SO_2NR^7R^8$, —$OSO_2NR^7R^8$ and pseudohalogen; and $R^3$ is selected from the formulae (iii)-(ix),

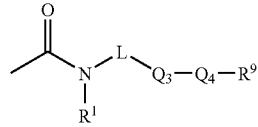

(iii)

-continued

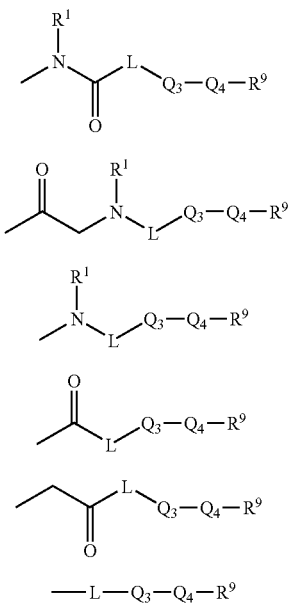

and

R$^4$ denotes a group selected from among hydrogen, —OR$^6$, —C(=O)R$^6$, —C(=O)OR$^6$, —C(=O)NR$^6$R$^7$, —NR$^6$R$^7$, —NR$^6$C(=O)R$^7$, —NR$^6$C(=O)OR$^7$, —NR$^6$C(=O)NR$^7$R$^8$, —NR$^6$SO$_2$R$^7$, —N=CR$^6$R$^7$, —SR$^6$, —SOR$^6$, —SO$_2$R$^6$, —SO$_2$NR$^6$R$^7$, —NR$^6$SO$_2$NR$^7$R$^8$, —OSO$_2$NR$^7$R$^8$ and pseudohalogen, or denotes a group selected from among optionally mono- or polysubstituted C$_{1-8}$-alkyl, C$_{2-10}$-alkenyl, C$_{2-10}$-alkynyl, C$_{3-8}$-cycloalkyl, aryl, heterocyclyl and heteroaryl, while the substituent(s) may be identical or different and are selected from among C$_{1-8}$-alkyl, halogen, —NO$_2$, —OR$^6$, —C(=O)R$^6$, —C(=O)OR$^6$, —C(=O)NR$^6$R$^7$, —NR$^6$R$^7$, —NR$^6$C(=O)R$^7$, —NR$^6$C(=O)OR$^7$, —NR$^6$C(=O)NR$^7$R$^8$, —NR$^6$SO$_2$R$^7$, —N=CR$^6$R$^7$, —SR$^6$, —SOR$^6$, —SO$_2$R$^6$, —SO$_2$NR$^6$R$^7$, —NR$^6$SO$_2$NR$^7$R$^8$, —OSO$_2$NR$^7$R$^8$ and pseudohalogen; and R$^5$ denotes hydrogen, halogen, —CF$_3$, C$_{1-3}$-alkyl or —OR$^6$; and R$^6$, R$^7$ and R$^8$ in each case independently of one another denote hydrogen or a group selected from among optionally mono- or polysubstituted C$_{1-5}$-alkyl, C$_{2-5}$-alkenyl, C$_{2-5}$-alkynyl, C$_{3-10}$-cycloalkyl, aryl, heterocyclyl and heteroaryl, while the substituent(s) may be identical or different and are selected from among C$_{3-10}$-cycloalkyl, aryl, heterocyclyl, heteroaryl, halogen, —NO$_2$, —OR$^{10}$, —C(=O)R$^{10}$, —C(=O)OR$^{10}$, —C(=O)NR$^{10}$R$^{11}$, —NR$^{10}$R$^{11}$, —NR$^{10}$C(=O)R$^{11}$, —NR$^{10}$C(=O)OR$^{11}$, —NR$^{10}$C(=O)NR$^{11}$R$^{12}$, —NR$^{10}$C(=O)ONR$^{11}$R$^{12}$, —NR$^{10}$SO$_2$R$^{11}$, —N=CR$^{10}$R$^{11}$, —SR$^{10}$, —SOR$^{10}$, —SO$_2$R$^{10}$, —SO$_2$NR$^{10}$R$^{11}$, —NR$^{10}$SO$_2$NR$^{11}$R$^{12}$, —OSO$_2$NR$^{10}$R$^{11}$ and pseudohalogen; and L denotes a bond or a group selected from among optionally mono- or polysubstituted C$_{1-16}$-alkyl, C$_{2-16}$-alkenyl, C$_{2-16}$-alkynyl, C$_{3-10}$-cycloalkyl, aryl, heterocyclyl and heteroaryl, while the substituent(s) may be identical or different and are selected from among halogen, —NO$_2$, —OR$^{10}$, —C(=O)R$^{10}$, —C(=O)OR$^{10}$, —C(=O)NR$^{10}$R$^{11}$, —NR$^{10}$R$^{11}$, —NR$^{10}$COR$^{11}$, —NR$^{10}$C(=O)OR$^{11}$, —NR$^{10}$C(=O)NR$^{11}$R$^{12}$, —NR$^{10}$C(=O)ONR$^{11}$R$^{12}$, —NR$^{10}$SO$_2$R$^{11}$, —N=CR$^{10}$R$^{11}$, —SR$^{10}$, —SOR$^{10}$, —SO$_2$R$^{10}$, —SO$_2$NR$^{10}$R$^{11}$, —NR$^{10}$SO$_2$NR$^{11}$R$^{12}$, —OSO$_2$NR$^{10}$R$^{11}$ and pseudohalogen; and Q$_3$ and Q$_4$ independently of one another denote a bond or a group selected from among optionally mono- or polysubstituted mono- or bicyclic heterocyclyl while the substituent(s) may be identical or different and are selected from among methyl, ethyl, halogen, —NH$_2$, —OH and pseudohalogen; and R$^9$ denotes a group selected from among optionally mono- or polysubstituted C$_{1-16}$-alkyl, C$_{2-16}$-alkenyl, C$_{2-16}$-alkynyl, C$_{3-10}$-cycloalkyl, aryl, heterocyclyl and heteroaryl, while the substituent(s) may be identical or different and are selected from among halogen, —NO$_2$, —OR$^{10}$, —C(=O)R$^{10}$, —C(=O)OR$^{10}$, —C(=O)NR$^{10}$R$^{11}$, —NR$^{10}$R$^{11}$, —NR$^{10}$COR$^{11}$, —NR$^{10}$C(=O)OR$^{11}$, —NR$^{10}$C(=O)NR$^{11}$R$^{12}$, —NR$^{10}$C(=O)ONR$^{11}$R$^{12}$, —NR$^{10}$SO$_2$R$^{11}$, —N=CR$^{10}$R$^{11}$, —SR$^{10}$, —SOR$^{10}$, —SO$_2$R$^{10}$, —SO$_2$NR$^{10}$R$^{11}$, —NR$^{10}$SO$_2$NR$^{11}$R$^{12}$, —OSO$_2$NR$^{10}$R$^{11}$ and pseudohalogen; and R$^{10}$, R$^{11}$ and R$^{12}$ in each case independently of one another denote hydrogen or a group selected from among optionally mono- or polysubstituted C$_{1-8}$-alkyl, C$_{2-8}$-alkenyl, C$_{2-8}$-alkynyl, C$_{3-10}$-cycloalkyl, aryl, heterocyclyl and heteroaryl, while the substituent(s) may be identical or different and are selected from among halogen, —NH$_2$, —OH and pseudohalogen;

optionally in the form of the tautomers, the racemates, the enantiomers, the diastereomers and the mixtures thereof, as well as optionally the pharmacologically acceptable acid addition salts thereof, and at least one other active substance selected from among cytostatic active substances, cytotoxic active substances, steroids and antibodies, optionally in the form of the tautomers, the racemates, the enantiomers, the diastereomers and the mixtures thereof, as well as optionally the pharmacologically acceptable acid addition salts thereof.

Definitions

As used herein, the following definitions apply, unless stated otherwise.

By alkyl substitutents are meant in each case saturated, straight-chain or branched aliphatic hydrocarbon groups (alkyl group).

The alkenyl substituents are in each case straight-chain or branched, unsaturated alkyl groups which have at least one double bond.

By alkynyl substituents are meant in each case straight-chain or branched, unsaturated alkyl groups which have at least one triple bond.

Haloalkyl refers to alkyl groups wherein one or more hydrogen atoms are replaced by halogen atoms. Haloalkyl includes both saturated alkyl groups and unsaturated alkenyl and alkynyl groups, such as for example —CF$_3$, —CHF$_2$, —CH$_2$F, —CF$_2$CF$_3$, —CHFCF$_3$, —CH$_2$CF$_3$, —CF$_2$CH$_3$, —CHFCH$_3$, —CF$_2$CF$_2$CF$_3$, —CF$_2$CH$_2$CH$_3$, —CF=CF$_2$, —CCl=CH$_2$, —CBr=CH$_2$, —CI=CH$_2$, —C≡C—CF$_3$, —CHFCH$_2$CH$_3$ and —CHFCH$_2$CF$_3$.

Halogen relates to fluorine, chlorine, bromine and/or iodine atoms.

By pseudohalogen are meant the following groups: —OCN, —SCN, —CF3 and —CN.

By cycloalkyl is meant a mono- or bicyclic ring, while the ring system may be a saturated ring or an unsaturated, non-aromatic ring, which may optionally also contain double bonds, such as for example cyclopropyl, cyclopropenyl, cyclobutyl, cyclobutenyl, cyclopentyl, cyclopentenyl, cyclohexyl, cyclohexenyl, norbornyl and norbornenyl.

Aryl relates to monocyclic or bicyclic rings with 6-12 carbon atoms such as for example phenyl and naphthyl.

By heteroaryl are meant mono- or bicyclic rings which contain instead of one or more carbon atoms one or more identical or different heteroatoms, such as e.g. nitrogen, sulphur or oxygen atoms. Examples include furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl and triazinyl. Examples of bicyclic heteroaryl groups are indolyl, isoindolyl, benzofuranyl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl and benzotriazinyl, indolizinyl, oxazolopyridinyl, imidazopyridinyl, naphthyridinyl, indolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroiso-coumarinyl, isoindolinonyl, benzodioxanyl, benzoxazolinonyl, pyrrolyl-N-oxide, pyrimidinyl-N-oxide, pyridazinyl-N-oxide, pyrazinyl-N-oxide, quinolinyl-N-oxide, indolyl-N-oxide, indolinyl-N-oxide, isoquinolyl-N-oxide, quinazolinyl-N-oxide, quinoxalinyl-N-oxide, phthalazinyl-N-oxide, imidazolyl-N-oxide, isoxazolyl-N-oxide, oxazolyl-N-oxide, thiazolyl-N-oxide, indolizinyl-N-oxide, indazolyl-N-oxide, benzothiazolyl-N-oxide, benzimidazolyl-N-oxide, pyrrolyl-AT-oxide, oxadiazolyl-N-oxide, thiadiazolyl-N-oxide, triazolyl-N-oxide, tetrazolyl-N-oxide, benzothiopyranyl-S-oxide and benzothiopyranyl-S,S-dioxide.

Heterocyclyl relates to 5-12 carbon atoms comprising saturated or unsaturated, non-aromatic mono-, bicyclic or bridged bicyclic rings, which carry heteroatoms, such as nitrogen, oxygen or sulphur, instead of one or more carbon atoms. Examples of such heterocylyl groups are tetrahydrofuranyl, pyrrolidinyl, pyrrolinyl, imidazolidinyl, imidazolinyl, pyrazolidinyl, pyrazolinyl, piperidyl, piperazinyl, indolinyl, isoindolinyl, morpholinyl, thiomorpholinyl, homomorpholinyl, homopiperidyl, homopiperazinyl, thiomorpholinyl-S-oxide, thiomorpholinyl-S,S-dioxide, pyrrolidinyl, tetrahydropyranyl, piperidinyl, tetrahydrothienyl, homopiperidinyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-S-oxide, tetrahydrothienyl-S,S-dioxide, homothiomorpholinyl-S-oxide, 2-oxa-5-azabicyclo[2.2.1]heptane, 8-oxa-3-aza-bicyclo[3.2.1]octane, 3,8-diaza-bicyclo[3.2.1]octane, 2,5-diaza-bicyclo[2.2.1]heptane, 3,8-diaza-bicyclo[3.2.1]octane, 3,9-diaza-bicyclo[4.2.1]nonane and 2,6-diaza-bicyclo[3.2.2]nonane.

The following Examples illustrate the present invention without restricting its scope:

Preparation of the Compounds According to the Invention

The compounds according to the invention may be prepared according to methods of synthesis A to C described hereinafter, wherein the substituents of general formulae (I to XVI) have the meanings given hereinbefore.

Chromatography:

For medium pressure chromatography (MPLC) silica gel made by Millipore (name: Granula Silica Si-60A 35-70 μm) or C-18 RP-silica gel made by Macherey Nagel (name: Polygoprep 100-50 C18) is used.

For high pressure chromatography (HPLC) columns made by Waters (name: XTerra Prep. MS C18, 5 μM, 30*100 mm or Symmetrie C18, 5 μm, 19*100) are used.

Mass Spectroscopy/UV Spectrometer:

These data are generated using an HPLC-MS apparatus (high performance liquid chromatography with mass detector) made by Agilent.

The apparatus is constructed so that a diode array detector (G1315B made by Agilent) and a mass detector (1100 LS-MSD SL; G1946D; Agilent) are connected in series downstream of the chromatography apparatus (column: Zorbax SB-C8, 3.5 μm, 2,1*50, Messrs. Agilent). The apparatus is operated with a flow of 0.6 ml/min. For a separation process a gradient is run through within 3.5 min (start of gradient: 95% water and 5% acetonitrile; end of gradient: 5% water and 95% acetonitrile; in each case 0.1% formic acid is added to the two solvents).

Where the preparation of the starting compounds is not described, they are known, commercially available or may be prepared analogously to known compounds or processes described herein. Unless otherwise stated, the compounds are in the form of the free base. In the Tables $X_1$ and $X_2$ denote the point of attachment of the particular structural fragment to the generic structural unit.

Method A

Step 1A

The intermediate compound III is prepared by substitution of a leaving group LG, for example halogen, pseudohalogen, methoxy, preferably chlorine, in a heteroaromatic system I by a nucleophile II.

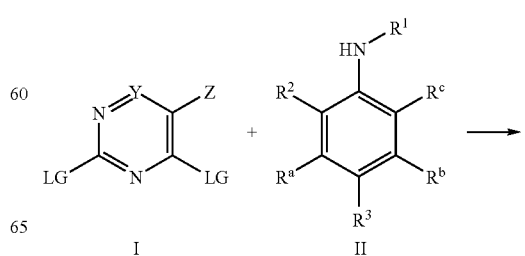

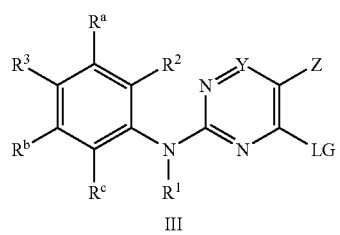

III oder:

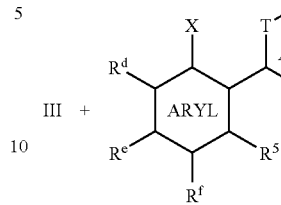

VI 1 equivalent of compound I and 1 to 1.5 equivalents of compound II are stirred in a solvent, for example 1,4-dioxane, tetrahydrofuran, N,N-dimethylformamide or N,N-dimethylacetamide.

At a temperature of 15 to 25° C., 2 to 2.5 equivalents of a base, for example potassium carbonate, sodium carbonate, caesium carbonate, N-ethyl-N,N-diisopropylamine or triethylamine, are added. The reaction mixture is stirred for a further 12 to 72 h at a temperature of 15 to 25° C. Then the solvent is distilled off and the residue is combined with water which has been adjusted to a pH of between 1-4 with an inorganic acid, for example hydrochloric acid or sulphuric acid. This mixture is extracted two to three times with an organic solvent, for example diethyl ether, ethyl acetate or dichloromethane. The combined organic extracts are dried and the solvent is distilled off. The residue is purified by chromatography.

Step 2A

The end compound V or VII is prepared by substitution of a leaving group LG, for example halogen, SCN, methoxy, preferably chlorine, in a heteroaromatic system III by a nucleophile IV or VI.

Diagram 2A

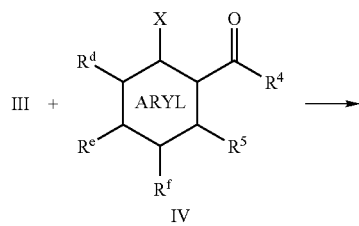

IV

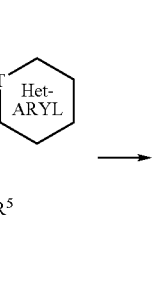

VII 1 equivalent of the compound III and 1 to 3 equivalents of the compound IV or VI are stirred in a solvent, for example 1,4-dioxane, N,N-dimethylformamide, N,N-dimethylacetamide or N-methyl-2-pyrrolidinone.

At a temperature of 15 to 40° C., 1 to 2 equivalents of an inorganic acid, for example sulphuric acid or hydrochloric acid, are added. The reaction mixture is stirred for another 12 to 72 h at a temperature of 20 to 100° C. Then the solvent is distilled off and the residue is purified by chromatography.

Method B

Step 1B

The intermediate compound IX is prepared by substitution of a leaving group LG, for example halogen, SCN, methoxy, preferably chlorine, in a heteroaromatic system I by a nucleophile VIII.

Diagram 1B

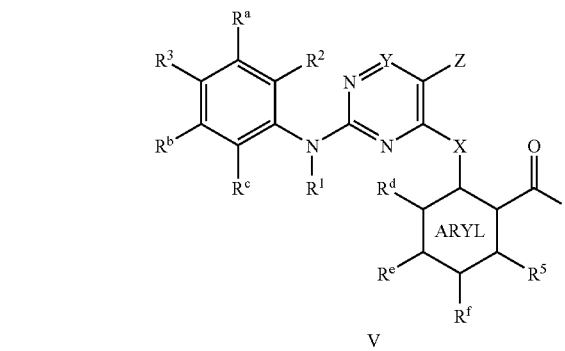

V

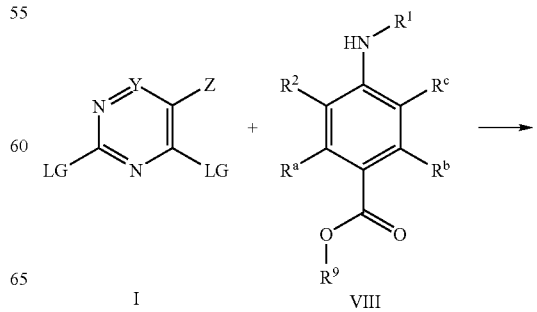

I        VIII

-continued

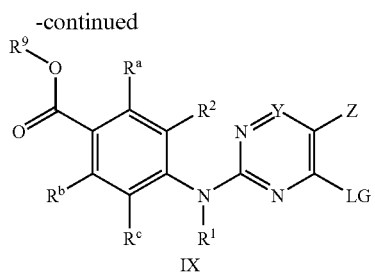

IX

-continued oder:

IX + 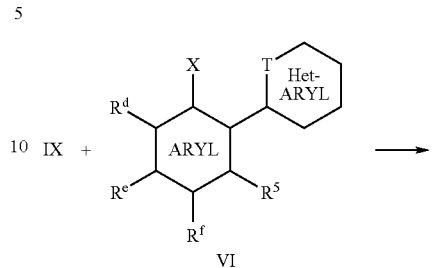

VI 1 equivalent of the compound I and 1 to 1.5 equivalents of the compound VIII are stirred in a solvent, for example 1,4-dioxane, tetrahydrofuran, N,N-dimethylformamide or N,N-dimethylacetamide.

At a temperature of 15 to 25° C., 2 to 2.5 equivalents of a base, for example potassium carbonate, sodium carbonate, caesium carbonate, potassium hydrogen phosphate, N-ethyl-N,N-diisopropylamine or triethylamine are added. The reaction mixture is stirred for 2 to 8 h more at a temperature of 50 to 120° C. The reaction mixture is combined with water, which has been adjusted to a pH of 8 to 9 with an inorganic base, for example sodium hydrogen carbonate or potassium carbonate. This mixture is extracted two to three times with an organic solvent, for example diethyl ether or ethyl acetate.

The combined organic extracts are dried and the solvent is distilled off. The residue is purified by repeated crystallisation.

Step 2B

The intermediate compound X or XI is prepared by substituting a leaving group LG, for example halogen, SCN, methoxy, preferably chlorine, in a heteroaromatic system IX by a nucleophile IV or VI.

Diagram 2B

IX + 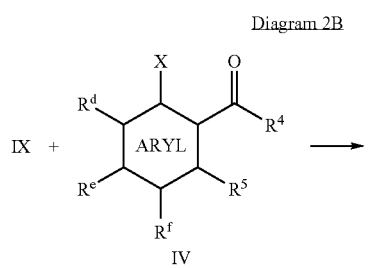

IV

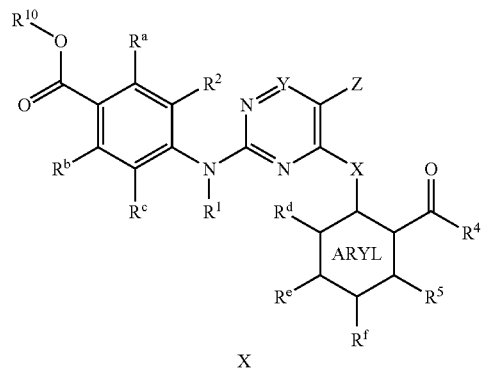

X

XI 1 equivalent of the compound IX and 1 to 1.5 equivalents of the compound IV or VI are stirred in a solvent, for example 1,4-dioxane, N,N-dimethylformamide, N,N-dimethylacetamide or N-methyl-2-pyrrolidinone.

At a temperature of 15 to 40° C., 0.2 to 1 equivalent of an acid, for example sulphuric acid or hydrochloric acid, is added. The reaction mixture is stirred for another 12 to 72 h at a temperature of 20 to 100° C. The reaction mixture is stirred into water and the resulting precipitate is filtered off and dried. The precipitate may be purified by chromatography or crystallisation or used as the crude product in the next step.

Step 3B

All the compounds X or XI having a group $R^{10}$ other than hydrogen must be converted into compounds wherein the group $R^{10}$ denotes hydrogen before the actual Step 3B by methods known from the literature. Compounds X or XI whose group $R^{10}$ denotes hydrogen may be used directly for preparing the end compounds XIII or XIV, while a compound XII is reacted with a compound X or XI.

Diagram 3B

X + 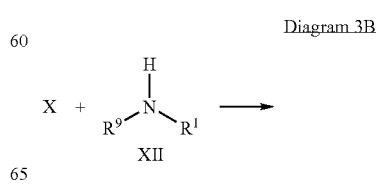

XII

-continued

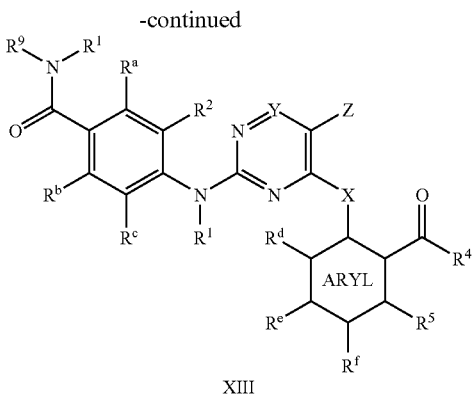

XIII oder:

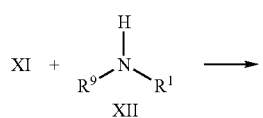

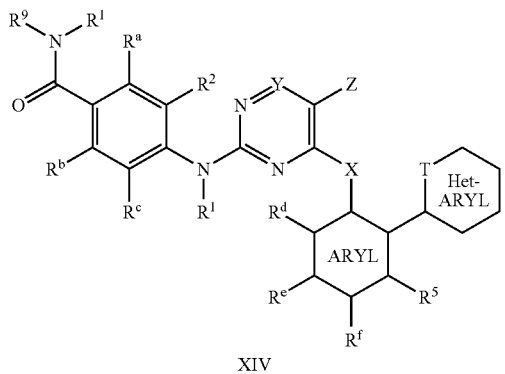

XIV 1 equivalent of the compound X or XI, 1 to 1.5 equivalents of the compound XII and 1 to 3 equivalents of a base, for example triethylamine or ethyldiisopropylamine, are stirred in a solvent, for example 1,4-dioxane, N,N-dimethylformamide, N,N-dimethylacetamide or N-methyl-2-pyrrolidinone.

At a temperature of 15 to 25° C. are 1 to 1.5 equivalents of a coupling reagent, for example N,N-dicyclohexylcarbodiimide, N,N-diisopropyl-carbodiimide, O-(benzotriazol-1-yl)-N,N,N',N'-tetramethyluronium-tetrafluoroborate or 1-(3-N,N-dimethylaminopropyl)-3-ethylcarbodiimide are added. The reaction mixture is stirred for another 4 to 24 h at a temperature of 15 to 25° C. Then the solvent is distilled off and the residue is purified by chromatography.

Method C

Step 1C

The intermediate compound XV or XVI is prepared by substituting a leaving group LG, for example halogen, SCN, methoxy, preferably chlorine, at a heteroaromatic system I with a nucleophilic group IV or VI.

Diagram 1C

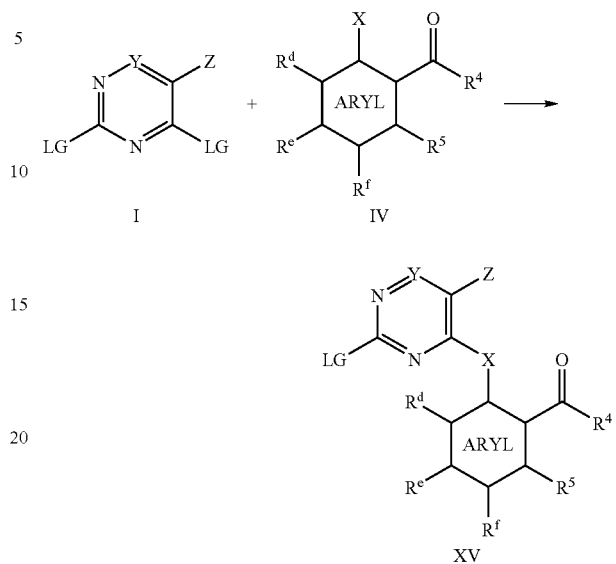

oder:

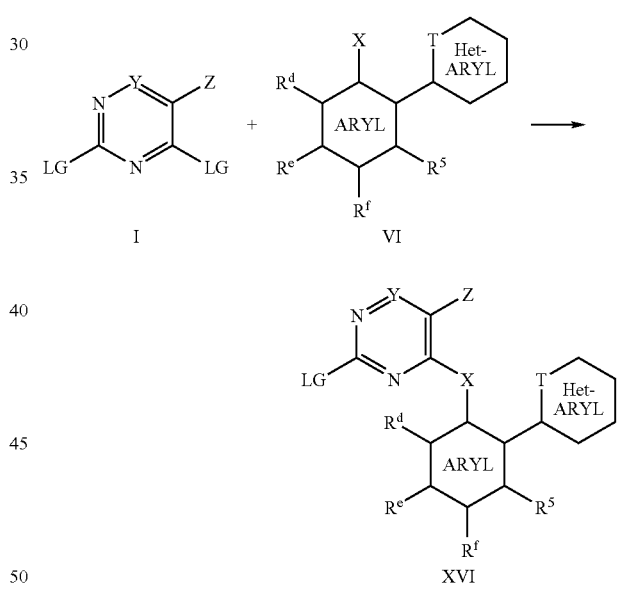

1 equivalent of the compound I and 1 to 3 equivalents of a base, for example triethylamine or ethyldiisopropylamine, are stirred in a solvent, for example 1,4-dioxane, tetrahydrofuran, N,N-dimethylformamide or N,N-dimethylacetamide. At a temperature of −60 to 0° C., 0.8 to 1.5 equivalents of a compound IV or VI are added. The reaction mixture is stirred for 12 to 72 h at a temperature of 15 to 25° C. Then the solvent is distilled off and the residue is purified by chromatography.

Step 2C

The end compound V or VII is prepared by substitution of a leaving group LG, for example halogen, SCN, methoxy, preferably chlorine, at a heteroaromatic system XV or XVI by a nucleophile II.

Diagram 2C

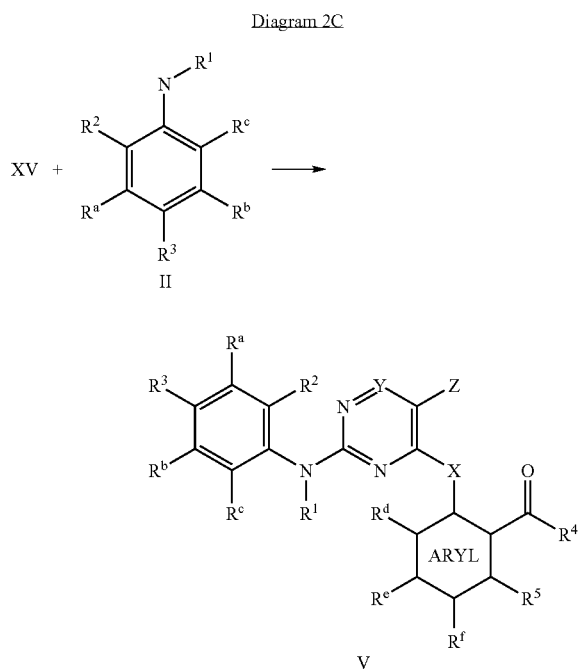

oder:

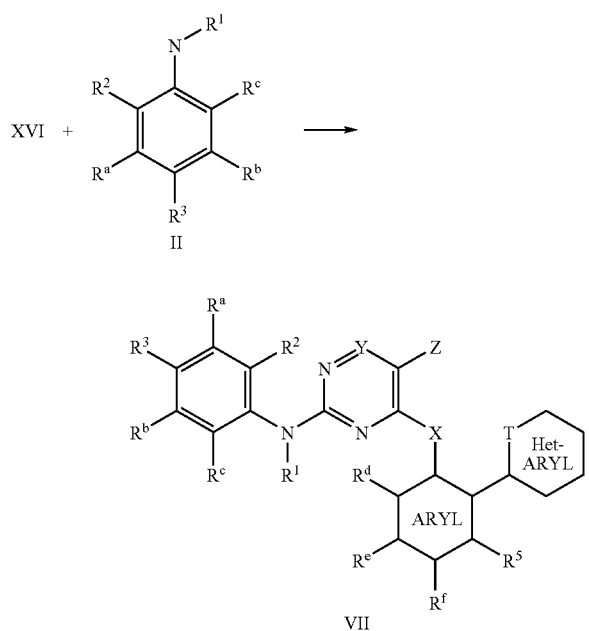

1 equivalent of the compound XV or XVI and 1 to 1.5 equivalents of the compound II are stirred in a solvent, for example 1,4-dioxane, N,N-dimethyl-formamide, N,N-dimethylacetamide or N-methyl-2-pyrrolidinone.

At a temperature of 15 to 40° C. 1 to 2 equivalents of an acid, for example sulphuric acid or hydrochloric acid, are added. The reaction mixture is stirred for another 12 to 72 h at a temperature of 20 to 100° C. Then the solvent is distilled off and the residue is purified by chromatography.

EXAMPLE 1

2-(2-methoxy-4-N-propylcarbamoyl-phenylamino)-4-(2-carboxy-3-fluoro-phenylamino)-5-trifluoromethyl-pyrimidine

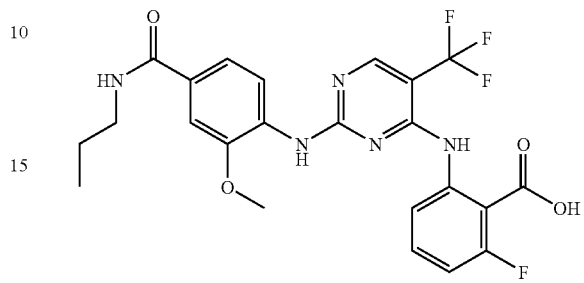

165 mg (0.424 mmol) 2-(2-methoxy-4-propylcarbamoyl-phenylamino)-4-chloro-5-trifluoro-methyl-pyrimidine (method 1) are dissolved in 400 µl 1,4-dioxane and combined with 72 mg (0.466 mmol) 2-amino-6-fluoro-benzoic acid. 106 µl of a 4 molar solution of HCl (0.424 mmol) in 1,4-dioxane are metered into this reaction mixture.

After one day at 50° C. the solvent is eliminated in vacuo. The crude product is purified by column chromatography. The carrier material used is silica gel and the eluent is dichloromethane to which 18% of a mixture of 90% methanol and 10% saturated aqueous ammonia solution have been added.

Yield: 212 mg (0.418 mmol; 98%) of a white solid UV max: 318 nm MS (ESI): 508 (M+H)⁺

EXAMPLES 2-10

The following compounds are prepared by an analogous method to that described in Example 1. 2-(2-Methoxy-4-propylcarbamoyl-phenylamino)-4-chloro-5-trifluoromethylpyrimidine and a corresponding commercially obtainable aniline are used. The solvent used is 1,4-dioxane, N-methyl-2-pyrrolidinone or N,N-dimethylacetamide.

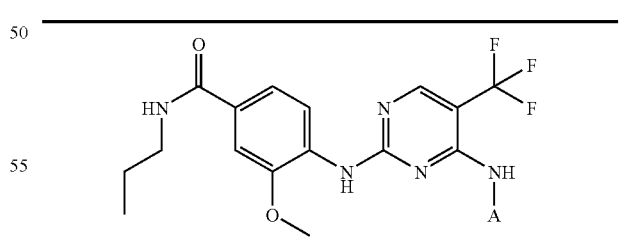

| # | A | UV max [nm] | MS (ESI) (M + H)⁺ |
|---|---|---|---|
| 2 | 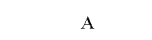 | 236/284 | 504 |

-continued

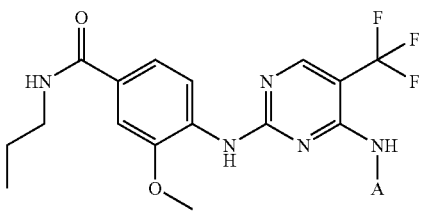

| # | A | UV max [nm] | MS (ESI) (M + H)+ |
|---|---|---|---|
| 3 | X₁-(2-methyl-6-benzoyl-phenyl) | 270 | 564 |
| 4 | X₁-(2-benzoyl-phenyl) | 322 | 550 |
| 5 | X₁-(2-formyl-phenyl) | 322 | 474 |
| 6 | X₁-(2-acetyl-phenyl) | 322 | 488 |
| 7 | X₁-(2-carbamoyl-phenyl) | 320 | 489 |
| 8 | X₁-(2-carbamoyl-6-fluoro-phenyl) | 314 | 507 |
| 9 | X₁-(2-carboxy-phenyl) | 322 | 490 |
| 10 | X₁-(2-acetyl-4,5-dimethoxy-phenyl) | 270 | 548 |

EXAMPLES 11-19

The following compounds are prepared by a method analogous to that described in Example 1.

The preparation of the corresponding aniline is described in Tetrahedron 2000, 56(37), 7245, Tetrahedron Letters 1992, 33(43), 6453, U.S. Pat. No. 4,307,113 or in method 2-5. 1,4-duixane or N,N-dimethylacetamide is used as solvent.

| # | X—A | UV max [nm] | MS (ESI) (M + H)+ |
|---|---|---|---|
| 11 | X₁-NH-(2-carbamoyl-3-methyl-phenyl) | 0 | 503 |
| 12 | X₁-NH-(2-(N-methylcarbamoyl)-phenyl) | 234 | 503 |
| 13 | X₁-NH-(2-carbamoyl-4-trifluoromethyl-phenyl) | 318 | 557 |
| 14 | X₁-NH-(2-(N,N-dimethylcarbamoyl)-phenyl) | 318 | 517 |
| 15 | X₁-N(methyl)-(2-carbamoyl-phenyl) | 318 | 503 |

-continued

| # | X—A | UV max [nm] | MS (ESI) (M + H)+ |
|---|---|---|---|
| 16 | 2-methylbenzohydrazide (N,N-dimethyl) with NH linker | 317 | 546 |
| 17 | 4,5-difluoro-2-amino-benzamide | 282 | 525 |
| 18 | 6-chloro-2-amino-benzamide | 318 | 523 |
| 19 | 6-trifluoromethyl-2-amino-benzamide | 318 | 557 |

EXAMPLES 20-33

The following compounds are prepared by a method analogous to that described in Example 1. 2-(2-Methoxy-4-propylcarbamoyl-phenylamino)-4-chloro-5-trifluoromethylpyrimidine and a corresponding aniline which is described in method 6 are used.

| # | A | UV max [nm] | MS (ESI) (M + H)+ |
|---|---|---|---|
| 20 | 2-fluoro-6-amino-N-(2-dimethylaminoethyl)benzamide | 320 | 578 |
| 21 | 2,6-difluoro-N,N-dimethylbenzamide | 275 | 535 |
| 22 | 2-fluoro-6-amino-N-(3-dimethylaminopropyl)benzamide | 320 | 592 |
| 23 | 2-fluoro-6-amino-N-(carbamoylmethyl)benzamide | 315 | 546 |
| 24 | 2-fluoro-6-amino-(4-methylpiperazin-1-yl)benzamide | 320 | 591 |
| 25 | 2-fluoro-6-amino-N-methylbenzamide | 315 | 521 |

-continued

[Structure: propyl-NH-C(O)-phenyl(OMe)-NH-pyrimidine(CF3)-NH-A]

| # | A | UV max [nm] | MS (ESI) (M + H)+ |
|---|---|---|---|
| 26 | 2-X₁-6-F-phenyl-C(O)NH-propyl | 318 | 549 |
| 27 | 2-X₁-6-F-phenyl-C(O)NH-benzyl | 315 | 597 |
| 28 | 2-X₁-6-F-phenyl-C(O)NH-(CH₂)₃-phenyl | 315 | 625 |
| 29 | 2-X₁-6-F-phenyl-C(O)NH-CH₂CH₂-phenyl | 318 | 612 |
| 30 | 2-X₁-6-F-phenyl-C(O)NH-CH₂CH₂-C(O)O-ethyl | 315 | 607 |
| 31 | 2-X₁-6-F-phenyl-C(O)O-CH₂-CH=CH-CH₂OH | 318 | 578 |
| 32 | 2-X₁-6-F-phenyl-C(O)NH-CH₂CH₂F | 316 | 553 |

| # | A | UV max [nm] | MS (ESI) (M + H)+ |
|---|---|---|---|
| 33 | 2-X₁-6-F-phenyl-C(O)NH-CH₂CF₃ | 230 | 589 |

EXAMPLES 34-41

The following compounds are prepared by a method analogous to that described in Example 1. 2-(2-Methoxy-4-propylcarbamoyl-phenylamino)-4-chloro-5-trifluoromethylpyrimidine and a corresponding aniline which is described in method 7 are used.

[Structure: propyl-NH-C(O)-phenyl(OMe)-NH-pyrimidine(CF3)-NH-A]

| # | A | UV max [nm] | MS (ESI) (M + H)+ |
|---|---|---|---|
| 34 | 2-X₁-6-(O-CH₂CH₂-NH₂)-phenyl-C(O)NH₂ | 282/318 | 548 |
| 35 | 2-X₁-6-OMe-phenyl-C(O)NH₂ | 314 | 519 |
| 36 | 2-X₁-6-OH-phenyl-C(O)NH₂ | 314 | 505 |

-continued

[Structure: N-propyl benzamide with methoxy and (pyrimidin-2-ylamino) substituents; pyrimidine bears 5-CF₃ and 4-NH-A]

| # | A | UV max [nm] | MS (ESI) (M + H)⁺ |
|---|---|---|---|
| 37 | [2-(X₁)-6-(OCH₂CH(NH₂)CH(CH₃)₂)oxy benzamide] | 230/282/318 | 590 |
| 38 | [2-(X₁)-6-(pyrrolidin-2-ylmethoxy)benzamide] | 230/282/318 | 588 |
| 39 | [2-(X₁)-6-(OCH₂CH(NH₂)CH₃)benzamide] | 282/318 | 562 |
| 40 | [2-(X₁)-6-(OCH₂CH(NH₂)CH₂CH(CH₃)₂)benzamide] | 226/282/318 | 604 |
| 41 | [2-(X₁)-6-(OCH(CH₃)CH₂NHCH₂CH(OH)CH₃)benzamide] | 226/282/318 | 620 |

EXAMPLES 42-45

The following compounds are prepared by a method analogous to that described in Example 1. 2-(2-Methoxy-4-propylcarbamoyl-phenylamino)-4-chloro-5-trifluoromethylpyrimidine and a corresponding aniline which is described in method 6 are used.

[Structure: N-propyl benzamide with methoxy and (pyrimidin-2-ylamino) substituents; pyrimidine bears 5-CF₃ and 4-NH-A]

| # | A | UV max [nm] | MS (ESI) (M + H)⁺ |
|---|---|---|---|
| 42 | [2-(X₁)-4-fluoro-benzamide] | 315 | 507 |
| 43 | [2-(X₁)-4-fluoro-N-(2-dimethylaminoethyl)benzamide] | 285/320 | 578 |
| 44 | [2-(X₁)-4-fluoro-N-(carbamoylmethyl)benzamide] | 230/285/320 | 564 |
| 45 | [2-(X₁)-4-fluoro-N-propyl-benzamide] | 318 | 549 |

EXAMPLES 46-48

The following compounds are prepared by a method analogous to that described in Example 1. 2-(2-Methoxy-4- propylcarbamoyl-phenylamino)-4-chloro-5-trifluoromethylpyrimidine and a corresponding aniline which is described in method 8 are used.

EXAMPLES 49-52

The following compounds are prepared by a method analogous to that described in Example 1. 2-(2-Methoxy-4-propylcarbamoyl-phenylamino)-4-chloro-5-trifluoromethylpyrimidine and a corresponding aniline which is described in method 9 are used.

| # | A | UV max [nm] | MS (ESI) (M + H)+ |
|---|---|---|---|
| 46 | (X₁-benzene-COO-ethyl) | 238/286 | 518 |
| 47 | (X₁-benzene-COO-isopropyl) | 230/282/306 | 532 |
| 48 | (X₁-benzene-COO-CH₂CH₂OH) | 282/318 | 534 |
| 49 | (X₁-benzene-CO-ethyl) | 280 | 502 |
| 50 | (X₁-benzene-CO-o-tolyl) | 230–330 | 564 |
| 51 | (X₁-benzene-CO-propyl) | 230 | 516 |
| 52 | (X₁-benzene-CO-isopropyl) | 270 | 516 |

EXAMPLES 53-56

The following compounds are prepared by a method analogous to that described in Example 1. 2-(2-Methoxy-4-propylcarbamoyl-phenylamino)-4-chloro-5-trifluoromethylpyrimidine and a corresponding aniline which is commercially obtainable or is described in the Journal of the Chemical Society, Perkin Transactions 1: 1979, (9), 2203 or in Journal of Medicinal Chemistry 1963, 6(5), 471-80 is used.

| # | A | UV max [nm] | MS (ESI) (M + H)+ |
|---|---|---|---|
| 53 | (X₁-benzene-CONH-CH₂CH₂OH) | 266 | 533 |

-continued

| # | A | UV max [nm] | MS (ESI) (M + H)+ |
|---|---|---|---|
| 54 | X₁—C(O)—N(piperidine) (ortho) | 316 | 557 |
| 55 | X₁—C(O)—N(piperazine) (ortho) | 313 | 556 (M − H) |
| 56 | X₁—C(O)—N(morpholine) (ortho) | 241, 250 | 559 |

EXAMPLE 57

2-[2-(2-chloro-phenoxy)-4-N-propylcarbamoyl-phenylamino]-4-(2-acetyl-phenylamino)-5-trifluoromethyl-pyrimidine

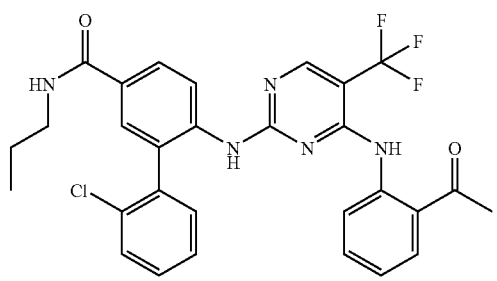

50 mg (0.16 mmol) 4-(2-acetyl-phenylamino)-2-chloro-5-trifluoromethyl-pyrimidine (method 10) are dissolved in 0.2 ml of 1,4-dioxane, combined with 60 mg (0.17 mmol) of 4-amino-3-(2-chloro-phenoxy)-N-propyl-benzamide hydrochloride (method 11) and stirred for 3 days at 50° C. Then the solvent is eliminated in vacuo and the crude product is purified by column chromatography, using C18 RP gel as carrier material. The product is eluted with a gradient which starts at water:acetonitrile=95%:5% and which changes within 20 min to a final ratio of water:acetonitrile=5%:95%.

Yield: 64 mg (0.088 mmol; 55%) of a yellow solid MS (ESI): 584/586 (M+H)+ isomer pattern ³⁵Cl/³⁷Cl UV max: 282 nm

EXAMPLES 58-63

The following compounds are prepared by a method analogous to that described in Example 57. 4-(2-Acetyl-phenylamino)-2-chloro-5-trifluoromethyl-pyrimidine and a corresponding aniline which is described in method 11 are used.

| # | R2 | UV max [nm] | MS (ESI) (M + H)+ |
|---|---|---|---|
| 58 | X₂—O—phenyl | 278 | 550 |
| 59 | X₂—O—(4-chlorophenyl) | 282 | 584 |
| 60 | X₂—O—(3-chlorophenyl) | 243 | 584 |
| 61 | X₂—O—ethyl | 318 | 502 |
| 62 | X₂—Br | 286 | 536 |

EXAMPLE 63

2-[2-methoxy-4-(4-morpholin-4-yl-(1,4-trans-cyclohexyl)carbamoyl)-phenylamino]-4-(2-carbamoyl-3-fluoro-phenylamino)-5-trifluoromethyl-pyrimidine

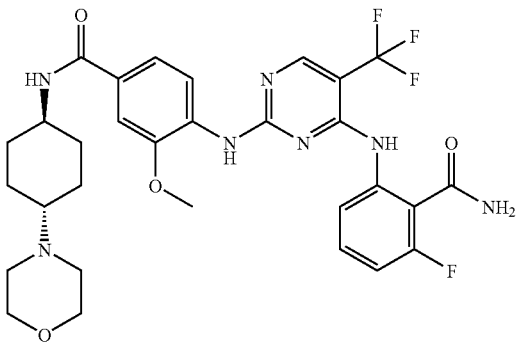

200 g (0.49 mmol) 2-(4-carboxyamino-2-methoxy-phenylamino)-4-chloro-5-trifluoromethyl-pyrimidine (method 12) are dissolved in 0.5 ml of N-methyl-2-pyrrolidinone and combined with 83 mg (0.54 mmol) 2-amino-6-fluoro-benzamide. 120 µl of a 4 M solution of HCl (0.49 mmol) in 1,4-dioxane are metered into this reaction mixture.

After 16 h at 90° C. the reaction mixture is stirred into 150 ml of 1 N aqueous hydrochloric acid. The precipitate is filtered off and dried in vacuo.

50 mg (0.11 mmol) of this precipitate, 94 µl (0.54 mmol) of N-ethyldiisopropylamine, 45 mg (0.13 mmol) TBTU and 30 mg (0.16 mmol) 4-(4-amino-cyclohexyl)-morpholine (method 13) are dissolved in 0.4 ml of tetrahydrofuran.

After 15 h at ambient temperature the solvent is eliminated in vacuo. The crude product is purified by column chromatography. The carrier material used is silica gel and the eluant is dichloromethane to which 5% of a mixture of 90% methanol and 10% saturated aqueous ammonia solution have been added.

Yield: 43 mg (0.068 mmol; 62%) of a light yellow solid
MS (ESI): 633 (M+H)$^+$

EXAMPLES 64–71

The following compounds are prepared by a method analogous to that described in Example 63. The corresponding aniline is described in method 6, 14 or 15. The amine used for the preparation of the amide is commercially obtainable or is described in method 13.

| # | A | R3 | UV max [nm] | MS (ESI) (M + H)$^+$ |
|---|---|----|-------------|----------------------|
| 64 | 2-acetyl-6-fluorophenyl (X$_1$, X$_2$) | n-butyl (X$_2$) | 284, 246 | 506 |
| 65 | 2-propanoyl-6-fluorophenyl (X$_1$, X$_2$) | n-butyl (X$_2$) | 243 | 520 |
| 66 | 2-butanoyl-6-fluorophenyl (X$_1$, X$_2$) | n-butyl (X$_2$) | 319 | 534 |
| 67 | 2-carbamoyl-6-fluorophenyl (X$_1$, X$_2$) | 1-methylpiperidin-4-yl (X$_2$) | 320 | 562 |

-continued
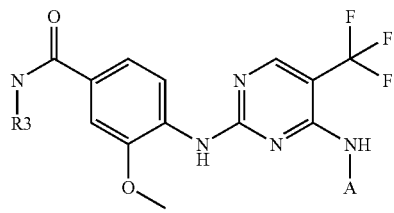
| # | A | R3 | UV max [nm] | MS (ESI) (M + H)+ |
|---|---|---|---|---|
| 68 | 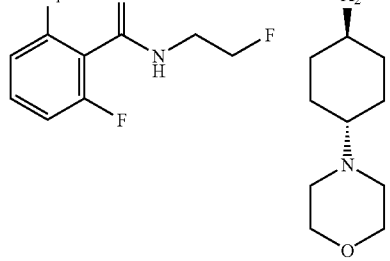 | | 318 | 678 |
| 69 | 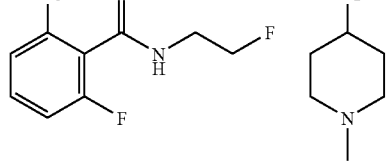 | | 318 | 608 |
| 70 | 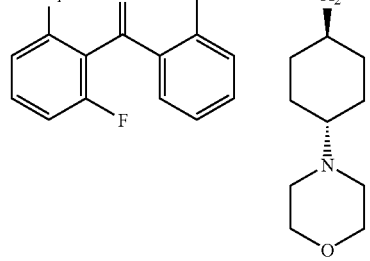 | | 314 | 707 |
| 71 | 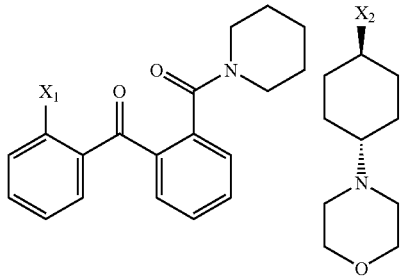 | | 318 | 786 |

EXAMPLES 72-76

The following compounds are prepared by a method analogous to that described in Example 1. 2-(2-Methoxy-4-propylcarbamoyl-phenylamino)-4-chloro-5-trifluoromethylpyrimidine and an aniline which is either commercially available or is described in method 6, 16 or 17 is used.

The solvent used is 1,4-dioxane, N-methyl-2-pyrrolidinone or N,N-dimethylacetamide.

| # | A | salt form | UV max [nm] | MS (ESI) (M + H)$^+$ |
|---|---|---|---|---|
| 72 | benzimidazol-2-yl-phenyl | base | 282, 322 | 562 |
| 73 | imidazol-2-yl-phenyl | base | 226, 278, 318 | 512 |
| 74 | N-methyl-N-(2-fluoroethyl)benzamide | base | 314, 283, 230 | 549 |
| 75 | furan-2-yl-phenyl | base | — | 512 |
| 76 | pyridin-2-yl-phenyl | base | 234, 274, 318 | 523 |

EXAMPLES 77-112

Following compounds are prepared by a method analogous to that described in Example 63. The corresponding aniline is commercially obtainable. The amine used to prepare the amide is commercially obtainable or is described in method 13 or 18.

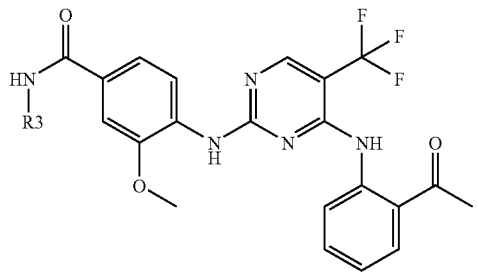
| # | R3 | salt form | UV max [nm] | MS (ESI) (M + H)+ |
|---|---|---|---|---|
| 77 | morpholine-cyclohexyl-NH-X₁ | dihydrochloride | 282, 318 | 613 |
| 78 | morpholinomethyl-cyclohexyl-NH-X₁ | dihydrochloride | 282, 318 | 627 |
| 79 | (CH₃)₂N-N(H)-X₁ | dihydrochloride | 286, 322 | 489 |
| 80 | (CH₃)₂N-CH₂CH₂CH₂-N(CH₃)-X₁ | base | | 545 |
| 81 | 1,2,2,6,6-pentamethylpiperidin-4-yl-NH-X₁ | base | | 599 |
| 82 | isopropyl-NH-X₁ | base | | 488 |
| 83 | (1H-imidazol-4-yl)ethyl-NH-X₁ | base | | 540 |

-continued
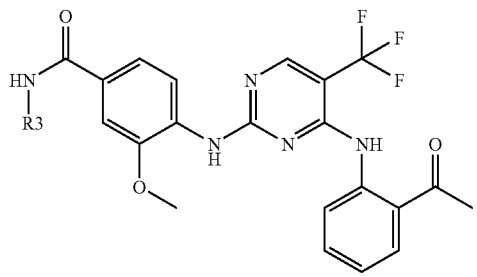
| # | R3 | salt form | UV max [nm] | MS (ESI) (M + H)+ |
|---|----|-----------|-------------|-------------------|
| 84 | morpholine-N-(CH2)3-NH-pyridine-NH-X1 | base | | 665 |
| 85 | Et2N-CH2CH2-piperazine-N-X1 | base | | 614 |
| 86 | MeO-CH2CH2-piperazine-N-X1 | base | | 573 |
| 87 | Et-NH-X1 | base | | 474 |
| 88 | morpholine-N-CH2CH2-piperazine-N-X1 | base | | 628 |
| 89 | pyrrolidine-N-(CH2)3-piperazine-N-X1 | base | | 626 |
| 90 | pyrrolidine-N-CH2CH2-NH-X1 | base | | 543 |

-continued
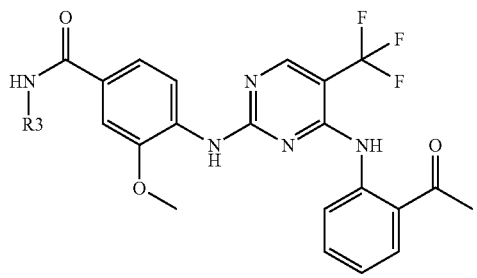
| # | R3 | salt form | UV max [nm] | MS (ESI) (M + H)+ |
|---|---|---|---|---|
| 91 | morpholine-propyl-NH-X₁ | base | | 573 |
| 92 | morpholine-propyl-NH-pyridyl-CH₂-NH-X₁ | base | | 679 |
| 93 | 2,3-dihydrobenzodioxine-CH₂-NH-X₁ | base | | 594 |
| 94 | HO-CH₂CH₂-O-CH₂CH₂-NH-X₁ | base | | 534 |
| 95 | HO-(CH₂)₃-NH-X₁ | base | | 504 |

-continued
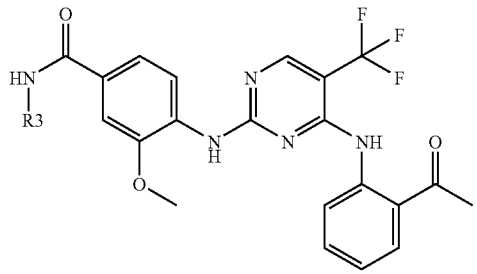
| # | R3 | salt form | UV max [nm] | MS (ESI) (M + H)+ |
|---|---|---|---|---|
| 96 | | base | | 572 |
| 97 | | base | | 613 |
| 98 | | base | | 554 |
| 99 | | base | | 559 |
| 100 | | base | | 586 |
| 101 | | base | | 557 |
| 102 | | base | | 543 |

-continued
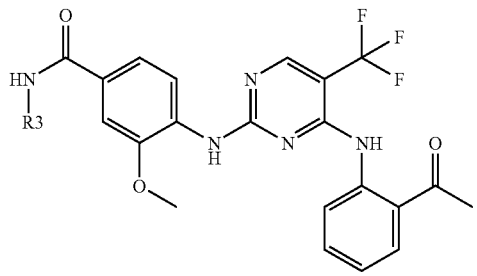
| # | R3 | salt form | UV max [nm] | MS (ESI) (M + H)+ |
|---|---|---|---|---|
| 103 | morpholine-CH2CH2-NH-pyridine-NH-X1 | base | | 651 |
| 104 | morpholine-CH2CH2-NH-pyridine-CH2-NH-X1 | base | | 665 |
| 105 | HO-CH2CH2-NH-X1 | base | | 490 |
| 106 | isobutyl-NH-X1 | base | | 502 |
| 107 | morpholine-CH2CH2-NH-X1 | base | | 559 |
| 108 | morpholine-CH2CH2CH2-piperazine-X1 | base | | 642 |
| 109 | morpholine-CH2CH2CH2-NH-pyrimidine-NH-X1 | base | | 666 |

-continued

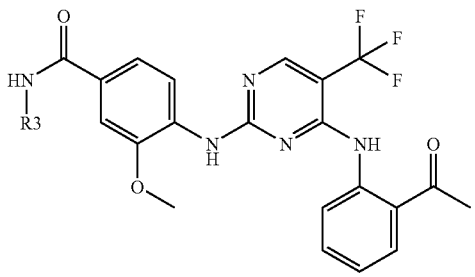

| # | R3 | salt form | UV max [nm] | MS (ESI) (M + H)+ |
|---|---|---|---|---|
| 110 | (morpholinyl-C(CH3)2-CH2-NH-X1) | base | | 587 |
| 111 | (quinuclidinyl-NH-X1) | base | | 555 |
| 112 | (morpholinyl-CH2CH2-NH-pyrimidinyl-NH-X1) | base | | 652 |

EXAMPLES 113–119

The following compounds are prepared by a method analogous to that described in Example 57. 4-(2-Acetyl-phenylamino)-2-chloro-5-trifluoromethyl-pyrimidine and a corresponding 5 aniline which is described in method 11 or 19 is used.

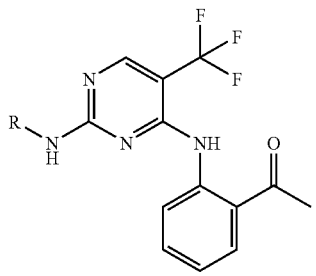

| # | R | salt form | UV max [nm] | MS (ESI) (M + H)+ |
|---|---|---|---|---|
| 113 | (3-CF3-4-X1-phenyl-C(O)NH-propyl) | base | 246 | 526 |

-continued
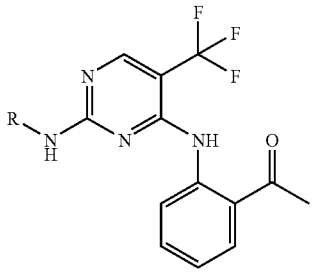
| # | R | salt form | UV max [nm] | MS (ESI) (M + H)+ |
|---|---|---|---|---|
| 114 | 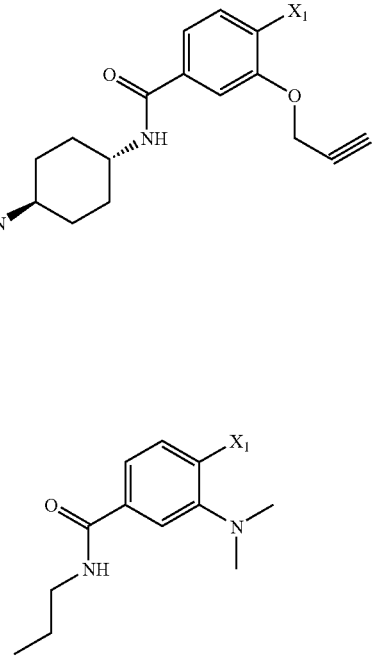 | dihydro-chloride | 226, 246, 282, 314 | 637 |
| 115 | 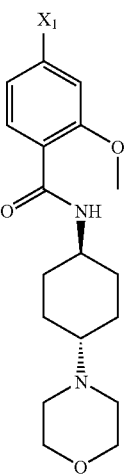 | base | 302 | 501 |
| 116 |  | diformate | 314 | 613 |

-continued
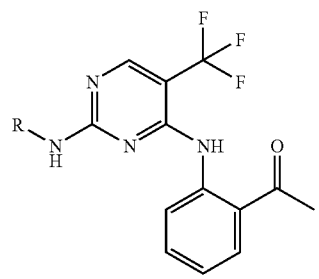
| # | R | salt form | UV max [nm] | MS (ESI) (M + H)+ |
|---|---|---|---|---|
| 117 | 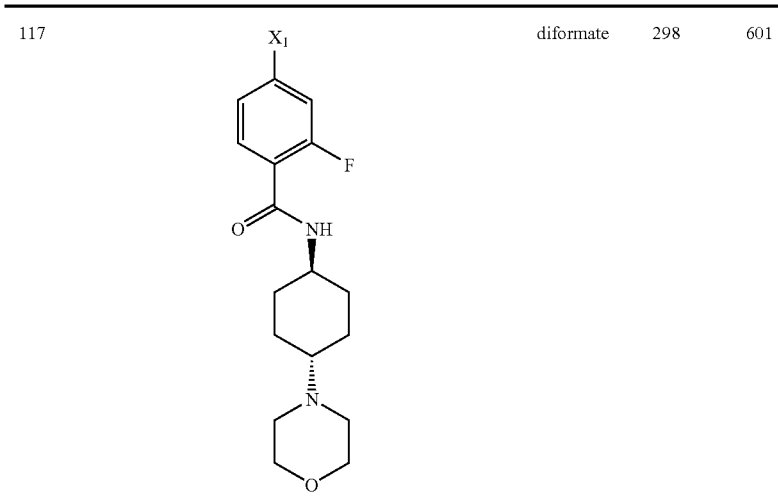 | diformate | 298 | 601 |
| 118 | 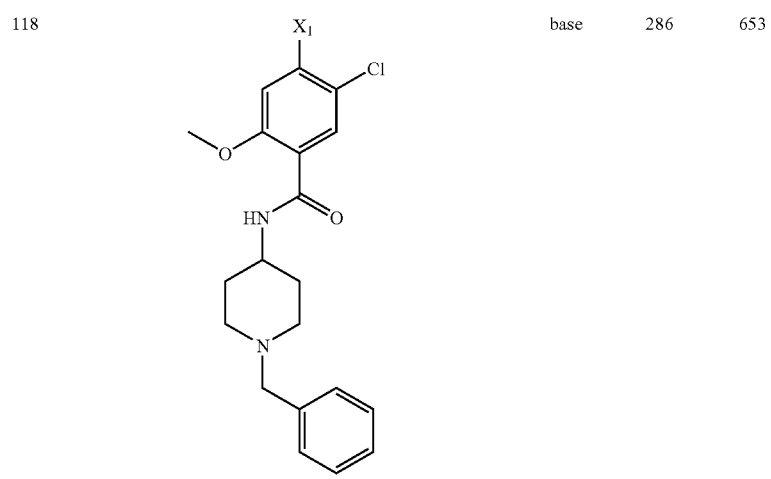 | base | 286 | 653 |
| 119 | 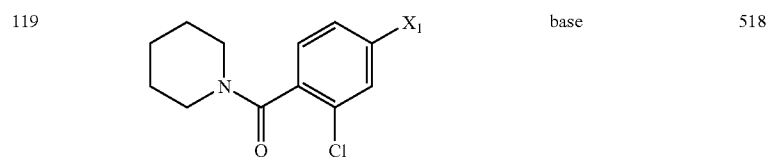 | base | | 518 |

EXAMPLES 120-144

The following compounds are prepared by a method analogous to that described in Example 63. The corresponding aniline is commercially obtainable or is described in method 6 or 20. The amine used to prepare the amide is commercially obtainable or is described in method 13.

| # | A | R3 | salt form | UV max [nm] | MS (ESI) (M + H)+ |
|---|---|---|---|---|---|
| 120 | 2-F,6-F benzamide-N-propyl-OH (X1) | N-methylpiperidin-4-yl (X2) | base | 316, 282, 234 | 620 |
| 121 | 2-F,6-F benzamide-N-propyl-OH (X1) | 4-morpholinocyclohexyl (X2) | base | 316, 282, 234 | 690 |
| 122 | 2-F,6-F benzamide-N-ethyl-OH (X1) | N-methylpiperidin-4-yl (X2) | base | 314, 278, 235 | 606 |
| 123 | 2-F,6-F benzamide-N-ethyl-OH (X1) | 4-morpholinocyclohexyl (X2) | base | 314, 278, 238 | 676 |
| 124 | 2-F,6-F benzamide-N-(2-hydroxyethyl) (X1) | 4-(morpholinomethyl)benzyl (X2) | base | 318, 282, 226 | 698 |

-continued
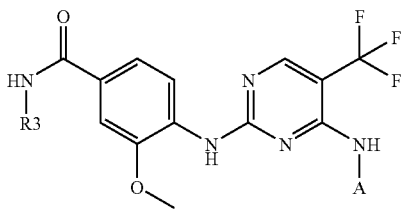
| # | A | R3 | salt form | UV max [nm] | MS (ESI) (M + H)+ |
|---|---|---|---|---|---|
| 125 | 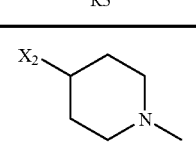 | 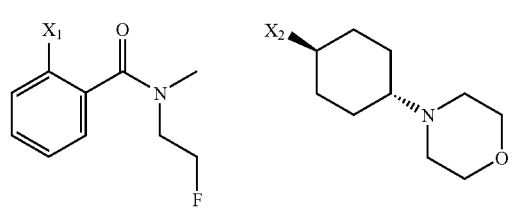 | hydrochloride | 316 | 604 |
| 126 | 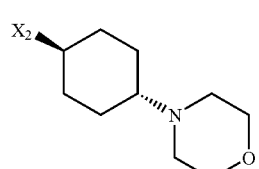 | 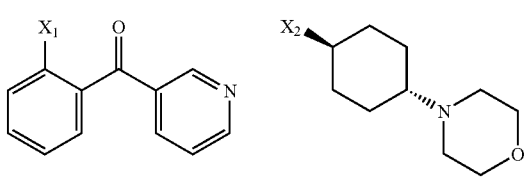 | dihydrochloride | 314 | 674 |
| 127 | 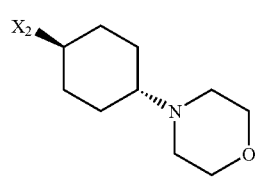 | 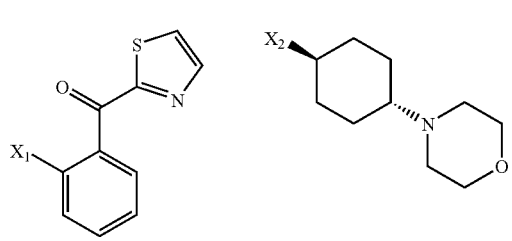 | base | 330 | 676 |
| 128 | 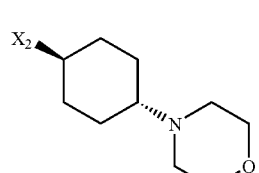 | 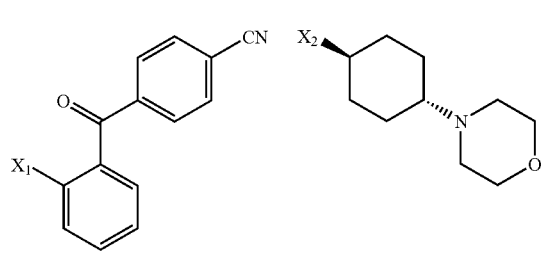 | base | 314 | 683 |
| 129 | 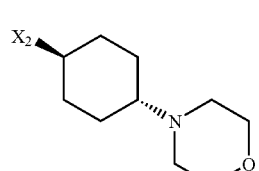 | 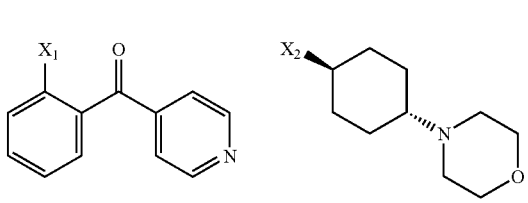 | base | 254 | 700 |
| 130 | 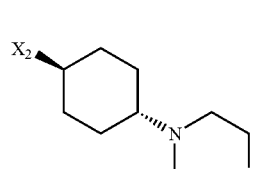 | | trihydrochloride | 316 | 676 |

-continued
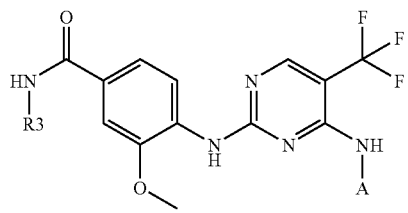
| # | A | R3 | salt form | UV max [nm] | MS (ESI) (M + H)+ |
|---|---|---|---|---|---|
| 131 | | | base | 313 | 671 (M − H)− |
| 132 | | | dihydro-chloride | 230, 282, 318 | 576 |
| 133 | | | dihydro-chloride | 278, 314 | 562 |
| 134 | | | trihydro-chloride | 230, 282, 318 | 685 |
| 135 | | | dihydro-chloride | 282, 318 | 562 |
| 136 | | | dihydro-chloride | 282, 318 | 576 |

-continued
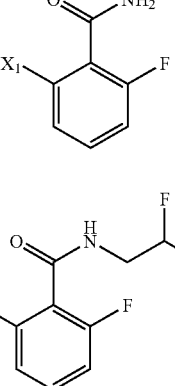
| # | A | R3 | salt form | UV max [nm] | MS (ESI) (M + H)+ |
|---|---|---|---|---|---|
| 137 | 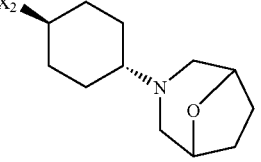 | 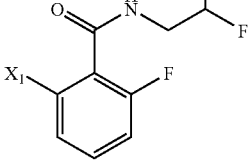 | dihydro-chloride | 282, 318 | 658 |
| 138 | 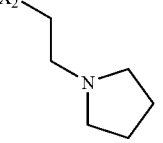 | 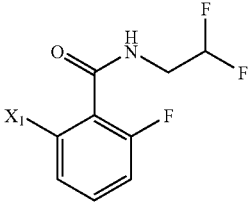 | dihydro-chloride | 226, 282, 318 | 626 |
| 139 | 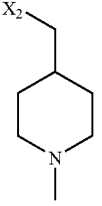 | 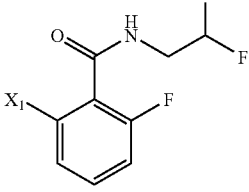 | dihydro-chloride | 230, 282, 318 | 640 |
| 140 | 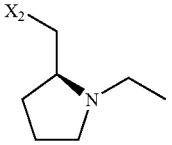 | 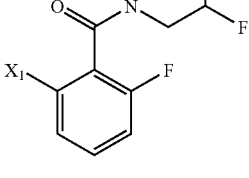 | dihydro-chloride | 230, 282, 322 | 640 |
| 141 | 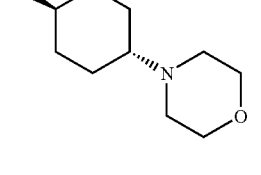 | 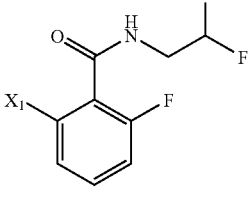 | dihydro-chloride | 230, 282, 318 | 696 |
| 142 | 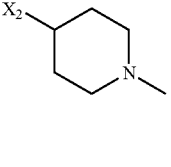 | | dihydro-chloride | 230, 282, 318 | 626 |

-continued

| # | A | R3 | salt form | UV max [nm] | MS (ESI) (M + H)+ |
|---|---|---|---|---|---|
| 143 | X₁-C₆H₄(o)-C(O)NH₂ | X₂-CH₂CH₂-pyrrolidinyl | dihydrochloride | 284, 325 | 544 |
| 144 | X₁-C₆H₄(o)-C(O)NH₂ | X₂-cyclohexyl-morpholinyl | dihydrochloride | 283, 317 | 614 |

Method 1

2-(2-methoxy-4-propylcarbamoyl-phenylamino)-4-chloro-5-trifluoromethyl-pyrimidine Method 2

2-amino-6-methyl-benzamide

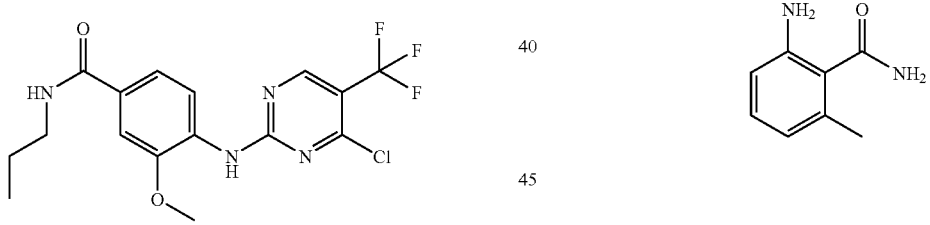

5 g (21.9 mmol) 2,4-dichloro-5-trifluoromethyl-pyrimidine are dissolved in 50 ml 1,4-dioxane and combined with 5.50 g (21.9 mmol) 4-amino-3-methoxybenzoic acid-propylamide hydrochloride (Journal of Pharmaceutical Sciences 1989, 78(10), 829-32). 7.50 ml (43.8 mmol) ethyldiisopropylamine are added to this reaction mixture and it is stirred for 2 days at ambient temperature. Then the reaction mixture is diluted with 250 ml of ethyl acetate and washed first of all with 300 ml aqueous 10% KHSO₄ solution, then with 300 ml saturated, aqueous NaCl solution. The organic phase is dried with MgSO₄ and the solvent is eliminated in vacuo.

The crude product is purified by column chromatography. The carrier material used is silica gel and the eluant is a mixture consisting of cyclohexane:ethyl acetate (75:25).

Yield: 2.30 g (5.9 mmol; 27%)

5.25 g (28.1 mmol) 2-methyl-6-nitrobenzoic acid are added to 250 ml of thionyl chloride and refluxed for 3 h. Then the thionyl chloride is eliminated in vacuo. Of the residue 2.93 g (14.7 mmol) are dissolved in 50 ml THF, cooled to 0° C. and combined with 44 ml of an aqueous, 32% ammonia solution. This reaction mixture is heated overnight with stirring to ambient temperature. Then the reaction mixture is diluted with 100 ml of ethyl acetate and washed three times with 50 ml of a saturated, aqueous NaCl solution. The organic phase is dried with MgSO₄ and the solvent is eliminated in vacuo.

2.44 g (13.5 mmol) of this reaction product are dissolved in 100 ml THF and combined with 200 mg Pd on charcoal (10% Pd). The reaction mixture is hydrogenated for 16 h at 3 bar H₂ pressure and ambient temperature. Then the catalyst is filtered off and the solvent is eliminated in vacuo.

Yield: 2.03 g (13.5 mmol; 48%)

The following compounds are prepared analogously to this method:

| | MS (ESI) (M + H)+ | | MS (ESI) (M + H)+ |
|---|---|---|---|
| 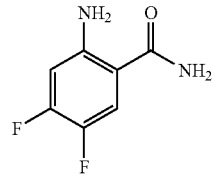 | 173 | 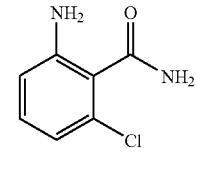 | 171 |

Method 3

2-methylamino-benzamide

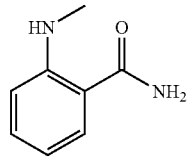

2 g (16.5 mmol) 2-fluorobenzonitrile are combined with 10 ml (80 mmol) of an 8 M methylamine solution in ethanol and heated for 20 h at 100° C. in a pressurised vessel. Then the reaction mixture is diluted with 200 ml of ethyl acetate and washed three times with 160 ml of an 10% NaCl solution. The organic phase is dried with $MgSO_4$ and the solvent is eliminated in vacuo.

1 g (7.6 mmol) of this reaction product are combined with 20 ml of 20% aqueous sulphuric acid and stirred for 3 h at 80° C. Then the reaction mixture is diluted with 200 ml of ethyl acetate and washed three times with 160 ml of aqueous 10% NaCl solution. Then the organic phase is dried with $MgSO_4$ and the solvent is eliminated in vacuo. The crude product is purified by column chromatography. The carrier material used is silica gel and the eluant is dichloromethane to which 15% of a mixture of 90% methanol and 10% saturated aqueous ammonia solution have been added.

Yield: 777 mg (5.2 mmol; 32%) MS (ESI): 151 (M+H)+

Method 4

2-amino-6-methyl-benzoic acid-N',N'-dimethyl-hydrazide

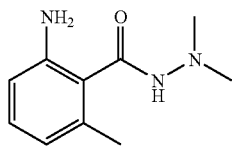

2-dimethylamino-7-nitro-2,3-dihydro-isoindol-1-one is prepared analogously to the compounds which are described in the Journal of the Chemical Society of Pakistan 1985, 7(1), 69-70, WO 03/14315 and U.S. Pat. No. 5,716,993.

240 mg (1.1 mmol) 2-dimethylamino-7-nitro-2,3-dihydro-isoindol-1-one are dissolved in 70 ml of dimethylformamide and 50 ml of methanol and combined with 100 mg Pd on charcoal (10% Pd). The reaction mixture is hydrogenated for 16 h at 3 bar $H_2$ pressure and ambient temperature. Then the catalyst is filtered off and the solvent is eliminated in vacuo.

Yield: 204 mg (1.0 mmol; 91%) MS (ESI): 194 (M+H)+

Method 5

2-amino-6-trifluoromethyl-benzamide

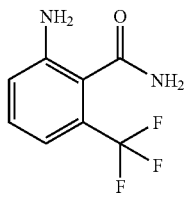

100 mg (0.5 mmol) 2-fluoro-6-trifluoromethyl-benzonitrile are combined with 1 ml of a 7 M ammonia solution in methanol and heated in the microwave for 20 min. at 100° C. Then the solvent is eliminated in vacuo, the crude product is combined with 1 ml of conc. $H_2SO_4$ and heated for 2.5 h at 80° C. Then the reaction mixture is stirred into ice water, neutralised with 1 M NaOH and extracted twice with 150 ml dichloromethane and three times with 160 ml of ethyl acetate. The organic phase is dried with $MgSO_4$ and the solvent is eliminated in vacuo. The crude product is purified by column chromatography. The carrier material used is silica gel and the eluant is dichloromethane, to which 4% of a mixture of 90% methanol and 10% saturated aqueous ammonia solution have been added.

Yield: 31 mg (0.152 mmol; 30%) MS (ESI): 205 (M+H)+

Method 6

2-amino-N-(2-dimethylamino-ethyl)-6-fluoro-benzamide

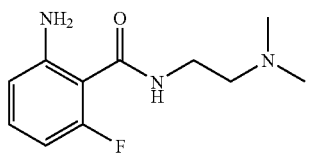

500 mg (3.2 mmol) 2-amino-6-fluorobenzoic acid, 284 μl (3.2 mmol) 2-N,N-dimethylaminoethylamine and 563 μl (3.2 mmol) diisopropylethylamine are dissolved in 2 ml of tetrahydrofuran and combined with 1.08 ml (3.2 mmol) TBTU. This reaction mixture is stirred for 2.5 h at ambient temperature. Then the reaction mixture is combined with 100 ml 10% aqueous potassium hydrogen carbonate solution and extracted six times with 100 ml of ethyl acetate. Then the organic phase is dried with $MgSO_4$ and the solvent is eliminated in vacuo.

The crude product is purified by column chromatography. The carrier material used is silica gel and the eluent used is dichloromethane, to which 8% of a mixture of 90% methanol and 10% saturated aqueous ammonia solution have been added.
Yield: 154 mg (21%) MS (ESI): 226 (M+H)⁺
The following compounds are prepared analogously to this method. 2-Amino-6-fluorobenzoic acid or 2-aminobenzoic acid and a corresponding commercially obtainable amine are used.
| | MS (ESI) (M + H)⁺ |
|---|---|
| 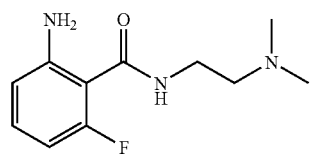 | 226 |
| 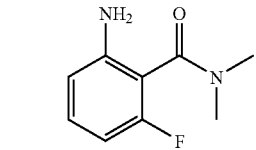 | 183 |
| 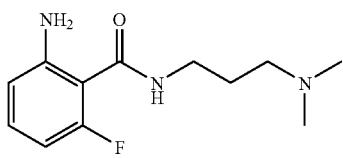 | 240 |
| 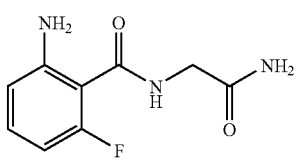 | 212 |
| 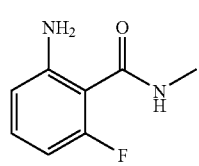 | 169 |
| 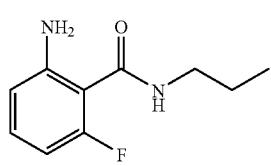 | 197 |
| 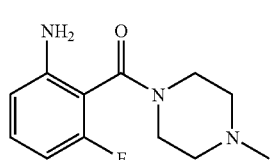 | 238 |
-continued
| | MS (ESI) (M + H)⁺ |
|---|---|
| 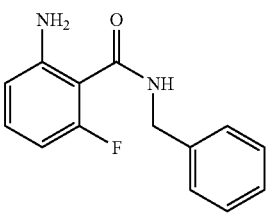 | |
| 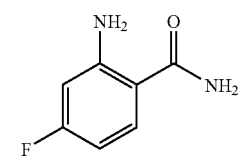 | |
| 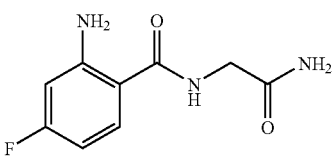 | |
| 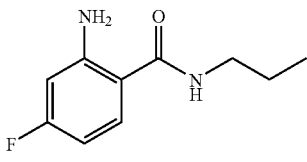 | |
| 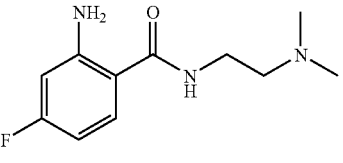 | |
| 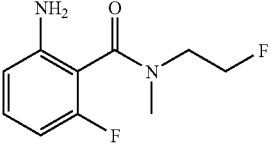 | 215 |
| 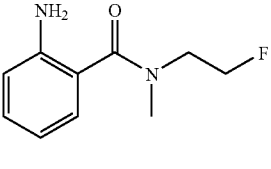 | 197 |
| 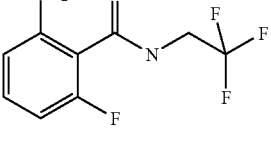 | 237 |

-continued

| | MS (ESI) (M + H)+ |
|---|---|
| 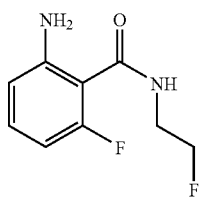 | 201 |
| 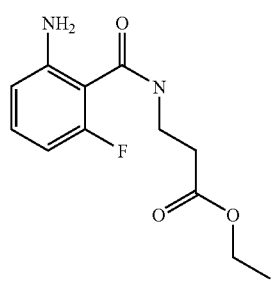 | |
| 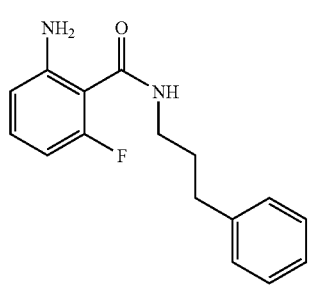 | |
| 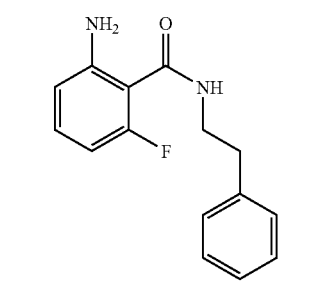 | 245 |
| 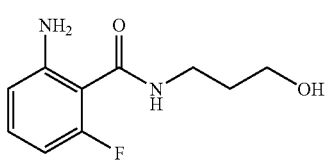 | 213 |
| 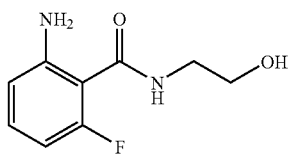 | 199 |
| 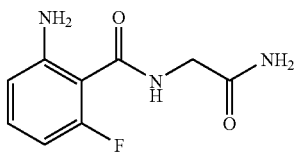 | 212 |

-continued

| | MS (ESI) (M + H)+ |
|---|---|
| 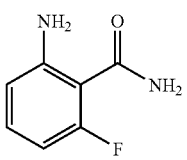 | 155 |
| 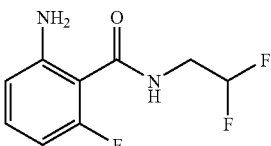 | 219 |

Method 7

2-amino-6-(2-amino-ethoxy)-benzamide

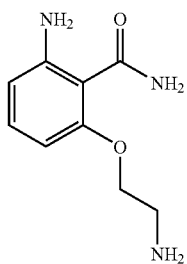

444 µl (7.4 mmol) ethanolamine are dissolved in 4 ml 1,4-dioxane, combined with 312 mg (7.8 mmol) sodium hydride and stirred for 30 min at ambient temperature. 1 g (7.4 mmol) 2-amino-6-fluorobenzonitrile are metered into this reaction mixture and it is stirred for 6 days at ambient temperature. Then the solvent is eliminated in vacuo. The crude product is purified by column chromatography. The carrier material used is silica gel and the eluant used is dichloromethane to which 10% of a mixture of 90% methanol and 10% saturated aqueous ammonia solution have been added.

434 mg (2.5 mmol) of the purified intermediate product are dissolved in 5 ml of a 20% potassium hydroxide solution in ethanol and stirred for 2 days at 90° C. Then the solvent is eliminated in vacuo.

The crude product is purified by column chromatography. The carrier material used is silica gel and the eluant used is dichloromethane to which 20% of a mixture of 90% methanol and 10% saturated aqueous ammonia solution have been added.

Yield: 164 mg (0.841 mmol; 11%) MS (ESI): 196 (M+H)+

The following compounds are prepared analogously to this method. 2-Amino-6-fluorobenzonitrile and a corresponding commercially obtainable alcohol are used.

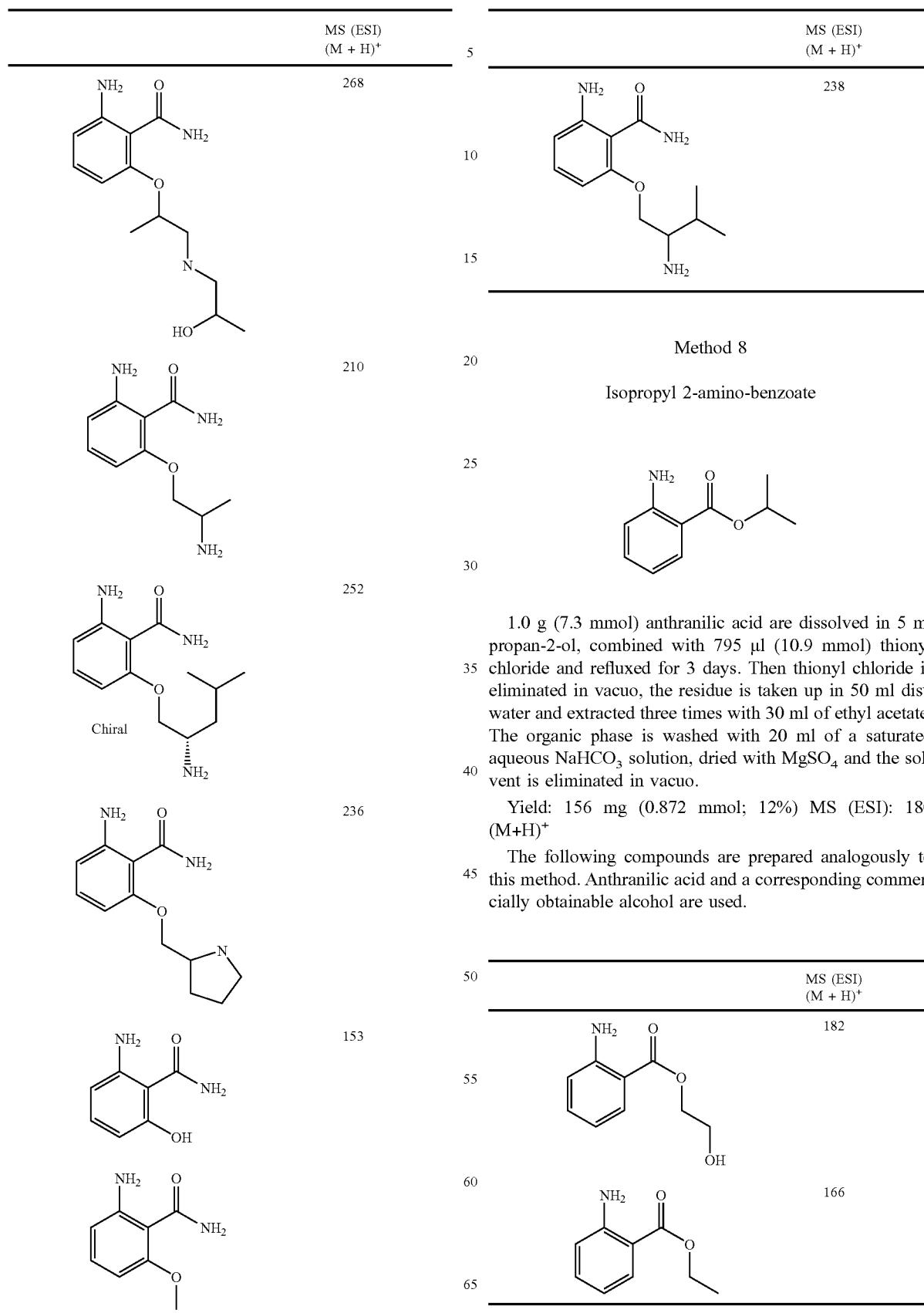

Method 8

Isopropyl 2-amino-benzoate 1.0 g (7.3 mmol) anthranilic acid are dissolved in 5 ml propan-2-ol, combined with 795 µl (10.9 mmol) thionyl chloride and refluxed for 3 days. Then thionyl chloride is eliminated in vacuo, the residue is taken up in 50 ml dist. water and extracted three times with 30 ml of ethyl acetate. The organic phase is washed with 20 ml of a saturated aqueous $NaHCO_3$ solution, dried with $MgSO_4$ and the solvent is eliminated in vacuo.

Yield: 156 mg (0.872 mmol; 12%) MS (ESI): 180 $(M+H)^+$

The following compounds are prepared analogously to this method. Anthranilic acid and a corresponding commercially obtainable alcohol are used.

Method 9

1-(2-amino-phenyl)-propan-1-one

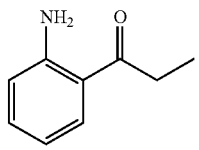

100 mg (0.6 mmol) N-(2-formyl-phenyl)-acetamide (Angew. Chem., Int. Ed. 2002, 41(16), 3028-31) are dissolved in 4 ml of tetrahydrofuran and cooled to −78° C. Then at this temperature 406 µl (1.2 mmol) of a 3 M solution of ethylmagnesium bromide in diethyl ether are added. This reaction mixture is left to come up to ambient temperature overnight with stirring. Then the reaction mixture is stirred into 30 ml dist. water and extracted three times with 10 ml of ethyl acetate. The organic phase is dried with MgSO$_4$, the solvent is eliminated in vacuo. The crude product is purified by column chromatography. The carrier material used is silica gel and the eluant used is a mixture of cyclohexane:ethyl acetate (1:1).

93 mg (0.5 mmol) of this intermediate product are dissolved in 6 ml dichloromethane, combined with 209 mg (2.4 mmol) manganese(IV)-oxide and stirred for 3 days at ambient temperature. Then the excess manganese(IV)-oxide is filtered through Celite and the solvent is eliminated in vacuo. The crude product is purified by column chromatography. The carrier material used is silica gel and the eluant used is a mixture of cyclohexane:ethyl acetate (85:15).

44 mg (0.23 mmol) of this intermediate product are dissolved in 2 ml of ethanol, combined with 4 ml of aqueous 1 N hydrochloric acid and stirred for 2 days at 40° C. Then the reaction mixture is stirred into 30 ml dist. water, adjusted to pH 7 with Na$_2$CO$_3$ and extracted three times with 10 ml of ethyl acetate. The organic phase is dried with MgSO$_4$ and the solvent is eliminated in vacuo.

Yield: 25 mg (0.168 mmol; 28%) MS (ESI): 150 (M+H)$^+$

The following compounds are prepared analogously to this method. N-(2-formyl-phenyl)-acetamide and a corresponding commercially obtainable Grignard compound are used as starting materials.

| | MS (ESI) (M + H)$^+$ |
|---|---|
| 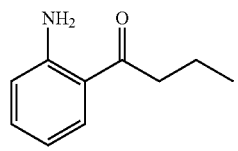 | 164 |
| 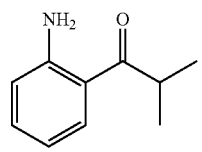 | 164 |
| 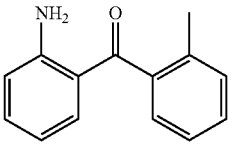 | 212 |

Method 10

4-(2-acetyl-phenylamino)-2-chloro-5-trifluoromethyl-pyrimidine

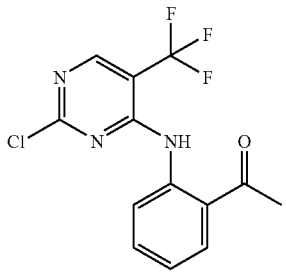

4.23 g (18.5 mmol) 2,4-dichloro-5-trifluoro-methyl-pyrimidine (J. Org. Chem. 1965, 30(3), 835) are dissolved in 2 ml of tetrahydrofuran, cooled to −40° C. and combined with 2.20 g (16.0 mmol) 2-aminoacetophenone and 7.77 ml (44.5 mmol) N-ethyldiisopropylamine. After 3 days at ambient temperature the solvent is eliminated in vacuo.

The crude product is purified by column chromatography. The carrier material used is silica gel and the eluant used is dichloromethane.

Yield: 1.38 g (4.4 mmol; 24%) MS (ESI): 316/318 (M+H)$^+$ Isotope distribution $^{35}$Cl/$^{37}$Cl

Method 11

4-amino-3-(2-chloro-phenoxy)-N-propyl-benzamide

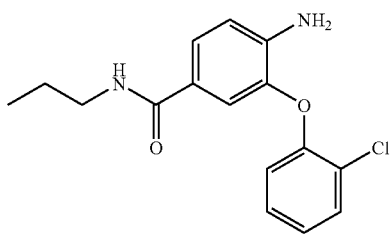

8.4 g (65.3 mmol) chlorophenol are dissolved in 60 ml N,N-dimethylformamide and combined with 5 g (36.2 mmol) potassium carbonate. The mixture is heated to 55° C. and 15 g (66.3 mmol) of 3-fluoro-4-nitro-N-propyl-benzamide dissolved in 20 ml N,N-dimethylformamide is added and stirred for 16 h at 55° C. The solvent is eliminated in vacuo and the residue is combined with 100 ml of water. The crystals formed are suction filtered and dried.

14 g (41.8 mmol) of this intermediate product are dissolved in 150 ml THF and combined with 1 g Raney nickel. The reaction mixture is stirred for 16 h at RT and 3 bar hydrogen pressure. Then the catalyst is filtered off and the solvent is eliminated in vacuo. The residue is taken up in butylmethylether and combined with 16 ml of a 5 molar solution of HCl (80 mmol) in isopropanol. The crystals are suction filtered and dried.

Yield: 13.5 g (44.4 mmol; 68%) MS (ESI): 305/307 (M+H)+ Isotope distribution $^{35}$Cl/$^{37}$Cl The following compounds are prepared analogously to this method.

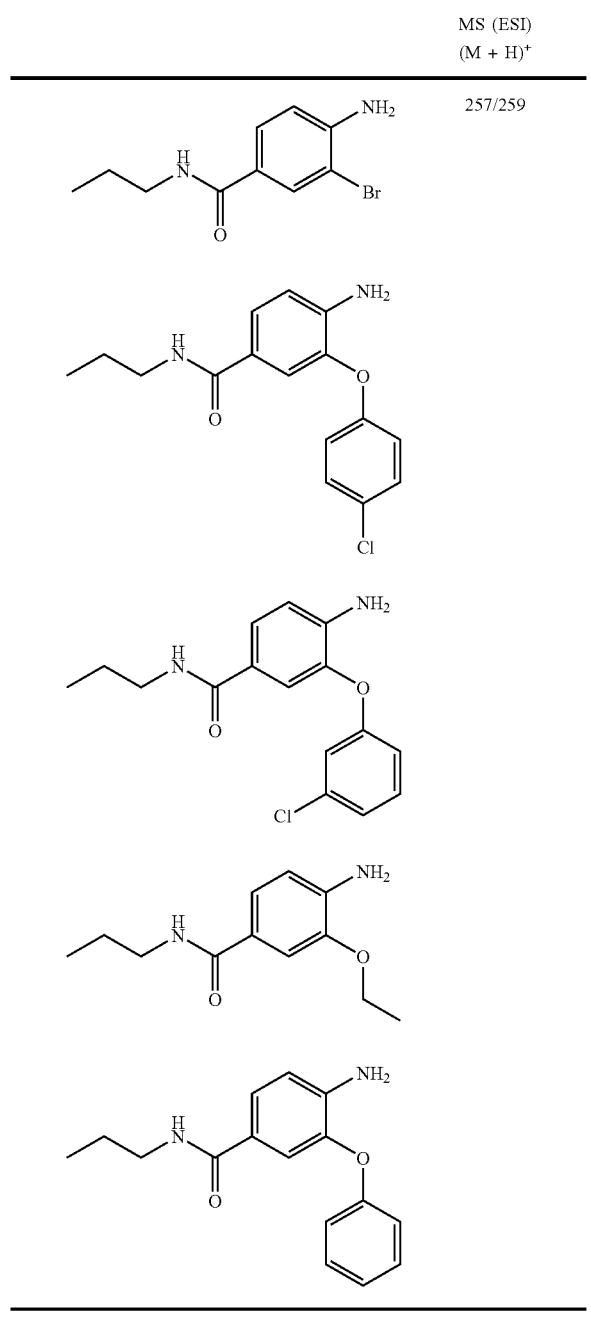

| | MS (ESI) (M + H)+ |
|---|---|
| | 257/259 |

Method 12

2-(4-carboxyamino-2-methoxy-phenylamino)-4-chloro-5-trifluoromethyl-pylimidine

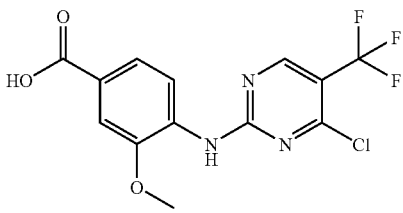

7.36 g (44 mmol) 4-amino-3-methoxybenzoic acid are suspended in 80 ml of an aqueous phosphate buffer solution (pH 6.3) and combined with 9.5 g (44 mmol) 2.4-dichloro-5-trifluoro-methyl-pyrimidine, which is dissolved in 240 ml 1,4-dioxane. After 4 h at 100° C. the reaction mixture is crystallised out at 0° C. The precipitate is filtered off, the filtrate is combined with 150 ml of ethyl acetate and washed twice with 200 ml of a saturated aqueous sodium hydrogen carbonate solution. The organic phase is dried with MgSO$_4$ and the solvent is eliminated in vacuo. The crude product is suspended in 10 ml n-hexane and refluxed. The precipitate is filtered off, suspended in 48 ml of a saturated aqueous sodium hydrogen carbonate solution and heated to 65° C. for 1 h. Then the solution is crystallised out at 0° C. The precipitate is filtered off, the filtrate is acidified with 1 N aqueous hydrochloric acid and combined with 100 ml of ethyl acetate. The organic phase is separated off, dried with magnesium sulphate and the solvent is eliminated in vacuo. The residue is recrystallised from ethyl acetate.

Yield: 330 mg (0.95 mmol, 2%) MS (ESI): 348 (M+H)+

Method 13

4-(4-amino-cyclohexyl)-morpholine

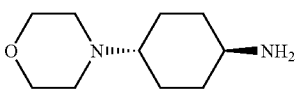

Dibenzyl-4-morpholino-cyclohexylamine 3.9 g (30 mmol)) 4-dibenzylcyclohexanone are dissolved in 100 mL dichloromethane and stirred with 3.9 g (45 mmol) morpholine and 9.5 g (45 mmol) sodium triacetoxyborohydride for 12 h at RT. Then the mixture is combined with water and potassium carbonate, the organic phase is separated off, dried and the solvent is eliminated in vacuo.

The crude product is purified by column chromatography. The carrier material used is silica gel and the eluant used is ethyl acetate to which 10% of a mixture of 90% methanol and 10% saturated aqueous ammonia solution have been added. The suitable fractions are evaporated down in vacuo.

Yield: 6.6 g (18 mmol, 60%) cis-isomer 2 g (5.4 mmol, 18%) trans-isomer trans-4-morpholino-cyclohexylamine 7.2 g (16.4 mmol) trans-dibenzyl-4-morpholino-cyclohexylamine are dissolved in 100 mL MeOH and hydrogenated on 1.4 g Pd/C (10%) at 30-50° C. The solvent is eliminated in vacuo and the residue is crystallised from ethanol and conc. HCl.

Yield: 3.9 g (15.2 mmol, 93%) melting point: 312° C.

Analogously to method 13 the following amines are prepared:

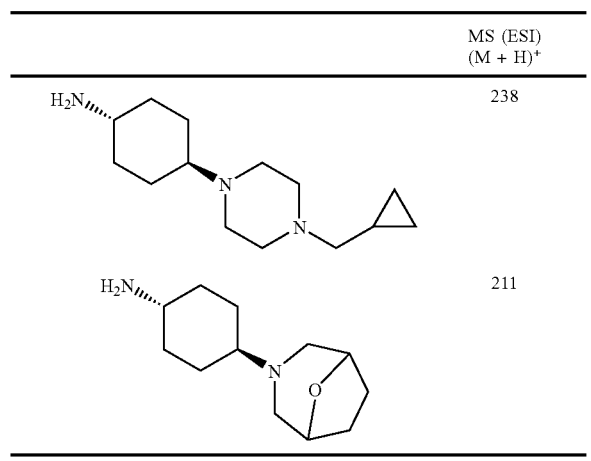

| | MS (ESI) (M + H)⁺ |
|---|---|
| H₂N—⟨cyclohexyl⟩—piperazine-CH₂-cyclopropyl | 238 |
| H₂N—⟨cyclohexyl⟩—8-oxa-3-azabicyclo | 211 |

Method 14

(2-amino-6-fluoro-phenyl)-o-tolyl-methanone

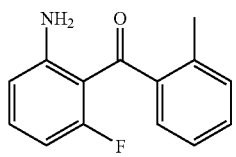

Methyl 2-amino-6-fluoro-benzoate 5 g (31.6 mmol) 2-amino-6-fluorobenzoic acid are dissolved in 50 ml of methanol and combined with 7.9 ml (31.6 mmol) of a 4 M solution of HCL in 1,4-dioxane and stirred for 10 min. at ambient temperature. The reaction mixture is combined dropwise with 3.45 ml (47.4 mmol) thionyl chloride and refluxed for 3 h. Then the reaction mixture is neutralised with 150 ml of a saturated, aqueous NaHCO₃ solution and extracted four times with 100 ml of ethyl acetate. The organic phase is dried with MgSO₄ and the solvent is eliminated in vacuo.

Yield: 1.57 g (9.3 mmol, 29%)

(2-amino-6-fluoro-phenyl)-methanol 676.3 mg (17.8 mmol) lithium aluminium hydride are placed in 65 ml diethyl ether under an N₂ atmosphere and cooled to 0° C. 2.01 g (11.9 mmol) methyl 2-amino-6-fluoro-benzoate, dissolved in 65 ml diethyl ether, are slowly added dropwise thereto and the mixture is stirred for 2 h at 0° C. Then the reaction mixture is combined dropwise at 0° C. with 100 ml dist. H₂O. The aqueous phase is extracted twice with 100 ml diethyl ether. The combined organic phases are washed once with 100 ml of a saturated, aqueous NaCl solution, dried with MgSO₄ and the solvent is eliminated in vacuo.

Yield: 1.44 g (10.2 mmol, 86%)

2-amino-6-fluoro-benzaldehyde 1.44 g (10.2 mmol) (2-amino-6-fluoro-phenyl)-methanol are dissolved in 120 ml chloroform, combined with 4.43 g (51 mmol) manganese(IV)-oxide and stirred for 2 days at ambient temperature. Then excess manganese(IV)-oxide is filtered off through Celite and the solvent is eliminated in vacuo.

Yield: 1.36 g (9.78 mmol, 96%)

N-(3-fluoro-2-formyl-phenyl)-acetamide 1.37 g (9.85 mmol) 2-amino-6-fluoro-benzaldehyde are combined with 20 ml acetic anhydride and heated to 70° C. for 4 h. Then the reaction mixture is stirred into 200 ml dist. water, adjusted to pH 7 with Na₂CO₃ and extracted three times with 50 ml of ethyl acetate. Then the organic phase is dried with MgSO₄, the solvent is eliminated in vacuo. The crude product is purified by column chromatography. The carrier material used is silica gel and the eluant used is a mixture of cyclohexane:ethyl acetate (80:20).

Yield: 1.40 g (7.73 mmol, 79%)

N-[3-fluoro-2-(hydroxyl-o-tolyl-methyl)-phenyl]-acetamide 100 mg (0.83 mmol) N-(3-fluoro-2-formyl-phenyl)-acetamide are dissolved in 4 ml of tetrahydrofuran and cooled to −78° C. Then at this temperature 1.66 ml (3.3 mmol) of a 2 M solution of o-tolylmagnesium bromide in diethyl ether are added. This reaction mixture is thawed to ambient temperature overnight with stirring. Then the reaction mixture is stirred into 30 ml dist. water and extracted three times with 10 ml of ethyl acetate. The organic phase is dried with MgSO₄, the solvent is eliminated in vacuo. The crude product is purified by column chromatography. The carrier material used is silica gel and the eluant used is a mixture of cyclohexane:ethyl acetate (80:20).

Yield: 205 mg (0.75 mmol, 90%)

N-[3-fluoro-2-(2-methyl-benzoyl)-phenyl]-acetamide 205 mg (0.75 mmol) N-[3-fluoro-2-(hydroxyl-o-tolyl-methyl)-phenyl]-acetamide are dissolved in 9 ml chloroform, combined with 652 mg (7.5 mmol) manganese(IV)-oxide and stirred for 3 d at ambient temperature. Then excess manganese(IV)-oxide is filtered off through Celite and the solvent is eliminated in vacuo. The crude product is purified by column chromatography. The carrier material used is silica gel and the eluant used is a mixture of cyclohexane:ethyl acetate (80:20).

Yield: 142 mg (0.52 mmol, 70%)

(2-amino-6-fluoro-phenyl)-o-tolyl-methanone 142 mg (0.52 mmol) N-[3-fluoro-2-(2-methyl-benzoyl)-phenyl]-acetamide are dissolved in 2 ml of ethanol, combined with 2 ml of conc. hydrochloric acid and stirred for 4 h at 70° C. Then the reaction mixture is stirred into 30 ml dist. water, adjusted to pH 7 with sodium carbonate and extracted three times with 10 ml of ethyl acetate. Then the organic phase is dried with MgSO₄ and the solvent is eliminated in vacuo.

Yield: 1.40 g (7.73 mmol, 79%) MS (ESI): 230 (M+H)⁺

The following compounds are prepared analogously to this method.

| | MS (ESI) (M + H)⁺ |
|---|---|
| 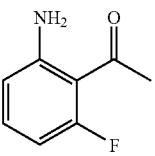 | 154 |
| 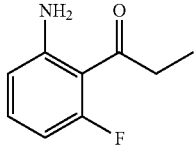 | 168 |
| 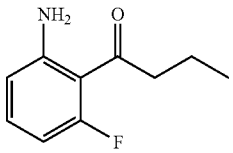 | 182 |

Method 15

(2-amino-phenyl)-[2-(piperidin-yl-1-carbonyl)-phenyl]-methanone

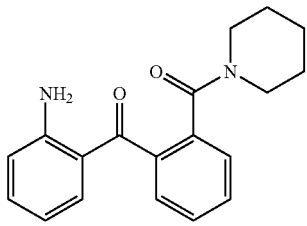

200 mg (0.81 mmol) 2-aminobenzophenone-2-carboxylic acid, 81 µl (0.81 mmol) piperidine and 425 µl (2.43 mmol) N-ethyldiisopropylamine are dissolved in 1 ml of tetrahydrofuran. 265 mg (0.81 mmol) TBTU are added to this reaction mixture and it is stirred overnight at ambient temperature. Then the reaction mixture is stirred into 20 ml dist. water and extracted three times with 5 ml of ethyl acetate. Then the organic phase is filtered through Alox B, dried with MgSO₄ and the solvent is eliminated in vacuo. The crude product is purified by column chromatography. The carrier material used is silica gel and the eluant used is dichloromethane to which 2% of a mixture of 90% methanol and 10% saturated aqueous ammonia solution have been added.

Yield: 89 mg (0.29 mmol, 36%) MS (ESI): 309 (M+H)⁺

Method 16

2-(1H-imidazol-2-yl)-phenylamine

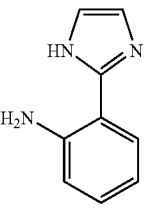

By catalytic hydrogenation, using palladium on charcoal or Raney Nickel as catalyst, 2-(2-nitro-phenyl)-1H-imidazole, which is commercially obtainable, is converted into 2-(1H-imidazol-2-yl)-phenylaamine (U.S. Pat. No. 6,376,664).

Method 17

2-furan-2-yl-phenylamine

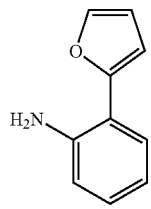

500 mg (2.43 mmol) 2-bromonitrobenzene are dissolved in 7.5 ml 1,4-dioxane under a protective gas atmosphere and combined with 2.5 ml of a 2 M sodium carbonate solution. Then 560 mg (4.86 mmol) furan-2-boric acid and 283 mg (0.243 mmol) tetrakis-(triphenylphosphine)-palladium(0) are added. The reaction mixture is stirred for 24 h under reflux conditions. The reaction mixture is cooled to ambient temperature and added to 100 ml of water. This mixture is extracted three times with 30 ml of ethyl acetate, the combined organic phases are dried with magnesium sulphate and the solvent is eliminated in vacuo. The crude product is purified by column chromatography. The carrier material used is silica gel and the eluant used is a mixture of cyclohexane:ethyl acetate (95:5).

Yield: 120 mg (0.63 mmol; 26%) MS (ESI): 190 (M+H)⁺

113 mg (0.6 mmol) 2-(2-nitro-phenyl)-furan are dissolved in 2 ml of ethanol and combined with 6 mg palladium on activated charcoal (10% Pd). 110 µl of a 35% aqueous hydrazine solution are added to this suspension and the reaction mixture is stirred for 20 h under reflux conditions. The catalyst is suction filtered, the filtrate is combined with 25 ml of water and adjusted to pH 5. This mixture is extracted three times with 10 ml of ethyl acetate. The combined organic phases are dried and the solvent is eliminated in vacuo.

Yield: 90 mg (0.57 mmol; 94%) MS (ESI): 160 (M+H)⁺

2-Pyridin-2-yl-phenylamine is prepared analogously to this method.

Method 18

4-morpholin-4-ylmethyl-cyclohexylamine

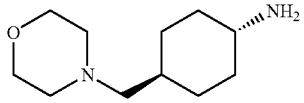

2.5 g (11.0 mmol) tert-butyl (4-formyl-cyclohexyl)-carbamate are dissolved in 25 ml DMA and combined with 1 ml (11 mmol) morpholine and 0.7 ml acetic acid. To this mixture are added 2.40 g (11.3 mmol) sodium triacetoxyborohydride, which is dissolved in 12.5 ml DMA.

The reaction mixture is stirred for 16 h at ambient temperature. Then the reaction mixture is added to 250 ml 10% potassium hydrogen carbonate solution and extracted three times with 100 ml of ethyl acetate. The organic phases are combined, dried and then the solvent is eliminated in vacuo.

The residue is taken up in 20 ml dichloromethane and 20 ml trifluoroacetic acid and stirred for one h at ambient temperature. The solvents are eliminated in vacuo.

Yield: 4.22 g (9.9 mmol; 90%) (double trifluoroacetic acid salt) MS (ESI): 199 (M+H)$^+$

Method 19

4-amino-N-(4-morpholin-4-yl-cyclohexyl)-3-prop-2-ynyloxy-benzamide 6.09 g (30 mmol) 3-fluoro-4-nitro-benzoic acid chloride are dissolved in 36 ml dichloromethane and cooled to 0° C. To this solution are added at 0° C. 5.52 g (30 mmol) 4-(4-aminocyclohexyl)-morpholine which is dissolved in 10 ml dichloromethane and combined with 4.65 g (45 mmol) triethylamine. After 16 h at 0° C. the reaction mixture is poured onto water. The precipitate is suction filtered and dried.

Yield: 4.74 g (13.5 mmol; 45%) MS (ESI): 352 (M+H)$^+$ 17.6 g (0.05 mol) 3-fluoro-N-(4-morpholin-4-yl-cyclohexyl)-4-nitro-benzamide and 9 g (0.16 mol) propagylalcohol are placed in 150 ml DMF and combined with 10 g potassium carbonate. This reaction mixture is stirred for 35 h at 70° C.

Half the solvent is eliminated in vacuo. Then the reaction mixture is added to 10% potassium carbonate solution. The resulting precipitate is filtered off and dried.

Yield: 17.5 g (13.5 mmol; 90%) MS (ESI): 388 (M+H)$^+$ 38.7 g (0.1 mol) N-(4-morpholin-4-yl-cyclohexyl)-4-nitro-3-prop-2-ynyloxy-benzamide are dissolved in 400 ml of ethyl acetate and 25 ml of methanol. To this solution are added 75 g tin (II)chloride.3H$_2$O. The mixture is stirred for 16 h at 50° C. Then it is cooled to ambient temperature and 80 ml of conc. aqueous ammonia are added.

The precipitate is suction filtered and discarded. The filtrate is evaporated down in vacuo. This residue is recrystallised from acetonitrile (1 g:20 ml). A by-product is precipitated which is also discarded. The filtrate is combined with 30 ml 1-chlorobutane and cooled to 10° C. The resulting precipitate is filtered off and dried.

Yield: 15.4 g (0.04 mmol; 43%) MS (ESI): 358 (M+H)$^+$

The following compounds are prepared analogously to this method. The reduction of the nitro group may optionally also be carried out with Pd/C or Raney nickel.

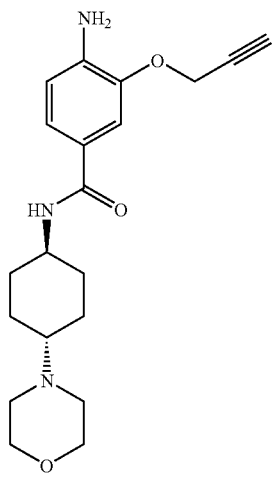

| | MS (ESI) (M + H)$^+$ |
|---|---|
| | 334 |
| | 322 |
| | 368/370 |
| | 239/241 |

Method 20

4-(2-amino-benzoyl)-benzonitrile

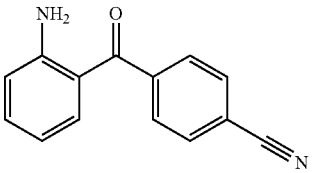

3.43 ml (5.50 mmol) of a 1.6 M solution of n-butyllithium in hexane are combined with 10 ml dry THF and cooled to −80° C. A solution of 1 g (5.94 mmol) 4-bromobenzonitrile in 10 ml THF are added dropwise to the butyllithium solution over a period of 30 min. After the reaction mixture has been stirred for a further 30 min at −80° C., 0.42 g (2.75 mmol) 2-nitrobenzaldehyde dissolved in 10 ml THF are added dropwise. After the addition, the mixture is stirred for a further 2 h at −80° C. Then saturated ammonium chloride solution is added. The organic phase is separated off, washed with water and dried. The solvent is eliminated in vacuo. The crude product is purified by column chromatography. The carrier material used is silica gel and the eluant used is a mixture of cyclohexane:ethyl acetate (2:1).

Yield: 0.59 (2.32 mmol; 42%) MS (ESI): 255 (M+H)$^+$

The other synthesis steps which lead to 4-(2-amino-benzoyl)-benzonitrile may be carried out analogously to method 9.

The following compounds are prepared analogously to this method:

| | MS (ESI) (M + H)$^+$ |
|---|---|
| [2-aminophenyl 2-pyridyl ketone] | 199 |
| [2-aminophenyl 3-pyridyl ketone] | 199 |
| [2-aminophenyl 4-pyridyl ketone] | 199 |
| [2-aminophenyl 2-thiazolyl ketone] | 205 |

Biological Properties

As demonstrated by DNA staining followed by FACS analysis, the inhibition of proliferation brought about by the compounds according to the invention is mediated above all by the arrest of the cells in the G2/M phase of the cell cycle. The cells arrest, depending on the type of cell used, for a specific length of time in this cell cycle phase before programmed cell death is initiated. An arrest in the G2/M phase of the cell cycle may be initiated e.g. by the inhibition of specific cell cycle kinases. On the basis of their biological properties the compounds of general formula I according to the invention, their isomers and the physiologically acceptable salts thereof are suitable for treating diseases characterised by excessive or anomalous cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tmours; skin diseases (e.g. psoriasis); bone diseases; cardiovascular diseases (e.g. restenosis and hypertrophy). They are also useful for protecting proliferating cells (e.g. hair, intestinal, blood and progenitor cells) from DNA damage caused by radiation, UV treatment and/or cytostatic treatment (Davis et al., 2001).

For example, the following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormon) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon, anus, small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; gall bladder cancer such as for example Klatskin tumour; testicular cancer such as for example seminomas and non-seminomas; lymphoma (lymphosarcoma) such as for example malignant lymphoma, Hodgkin's disease, non- Hodgkin's lymphomas (NHL) such as chronic lymphatic leukaemia, leukaemic reticuloendotheliosis, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, giant cell tumour, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypemephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma such as for example vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

The new compounds may be used for the prevention, short-term or long-term treatment of the above-mentioned diseases, also optionally in combination with other "state-of-the-art" compounds, such as other anti-tumour substances, cytotoxic substances, cell proliferation inhibitors, anti-angiogenic substances, steroids or antibodies.

The compounds of general formula (1) may be used on their own or in combination with other active substances according to the invention, optionally also in combination with other pharmacologically active active substances.

Chemotherapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortinsone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosinekinase inhibitors, such as for example gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

PLK-1 Kinase Assay

Recombinant human PLK1 enzyme linked to GST at its N-terminal end is isolated from insect cells infected with baculovirus (Sf21). Purification is carried out by affinity chromatography on glutathione sepharose columns.

$4 \times 10^7$ Sf21 cells (*Spodoptera frugiperda*) in 200 ml of Sf-900 II Serum free insect cell medium (Life Technologies) are seeded in a spinner flask. After 72 hours' incubation at 27° C. and 70 rpm, $1 \times 10^8$ Sf21 cells are seeded in a total of 180 ml medium in a new spinner flask. After another 24 hours, 20 ml of recombinant Baculovirus stock suspension are added and the cells are cultivated for 72 hours at 27° C. at 70 rpm. 3 hours before harvesting, okadaic acid is added (Calbiochem, final concentration 0.1 μM) and the suspension is incubated further. The cell number is determined, the cells are removed by centrifuging (5 minutes, 4° C., 800 rpm) and washed 1× with PBS (8 g NaCl/l, 0.2 g KCl/l, 1.44 g $Na_2HPO_4$/l, 0.24 g $KH_2PO4$/l). After centrifuging again the pellet is flash-frozen in liquid nitrogen. Then the pellet is quickly thawed and resuspended in ice-cold lysing buffer (50 mM HEPES pH 7.5, 10 mM $MgCl_2$, 1 mM DTT, 5 μg/ml leupeptin, 5 μg/ml aprotinin, 100 μM NaF, 100 μM PMSF, 10 mM β-glycerolphosphate, 0.1 mM $Na_3VO_4$, 30 mM 4-nitrophenylphosphate) to give $1 \times 10^8$ cells/17.5 ml. The cells are lysed for 30 minutes on ice. After removal of the cell debris by centrifugation (4000 rpm, 5 minutes) the clear supernatant is combined with glutathione sepharose beads (1 ml resuspended and washed beads per 50 ml of supernatant) and the mixture is incubated for 30 minutes at 4° C. on a rotating board. Then the beads are washed with lysing buffer and the recombinant protein is eluted from the beads with 1 ml eluting buffer/ml resuspended beads (eluting buffer: 100 mM Tris/HCl pH=8.0, 120 mM NaCl, 20 mM reduced glutathione (Sigma G-4251), 10 mM $MgCl_2$, 1 mM DTT). The protein concentration is determined by Bradford Assay.

Assay

The following components are combined in a well of a 96-well round-bottomed dish (Greiner bio-one, PS Microtitre plate No. 650101):

10 μl of the compound to be tested in variable concentrations (e.g. beginning at 300 μM, and dilution to 1:3) in 6% DMSO, 0.5 mg/ml casein (Sigma C-5890), 60 mM β-glycerophosphate, 25 mM MOPS pH=7.0, 5 mM EGTA, 15 mM MgCl$_2$, 1 mM DTT

20 µl substrate solution (25 mM MOPS pH=7.0, 15 mM MgCl$_2$, 1 mM DTT, 2.5 mM EGTA, 30 mM β-glycerophosphate, 0.25 mg/ml casein)

20 µl enzyme dilution (1:100 dilution of the enzyme stock in 25 mM MOPS pH=7.0, 15 mM MgCl$_2$, 1 mM DTT)

10 µl ATP solution (45 µM ATP with $1.11 \times 10^6$ Bq/ml gamma-P33-ATP).

The reaction is started by adding the ATP solution and continued for 45 minutes at 30° C. with gentle shaking (650 rpm on an IKA Schuittler MTS2). The reaction is stopped by the addition of 125 µl of ice-cold 5% TCA per well and incubated on ice for at least 30 minutes. The precipitate is transferred by harvesting onto filter plates (96-well microtitre filter plate: UniFilter-96, GF/B; Packard; No. 6005177), then washed four times with 1% TCA and dried at 60° C. After the addition of 35 µl scintillation solution (Ready-Safe; Beckmann) per well the plate is sealed shut with sealing tape and the amount of P33 precipitated is measured with the Wallac Betacounter.

The measured data are evaluated using the standard Graphpad software (Levenburg-Marquard Algorhythmus).

The activity of the compounds according to the invention is determined in the cytotoxicity test on cultivated human tumour cells and/or in a FACS analysis, for example on HeLa S3 cells. In both test methods the compounds exhibit goot to very good activity, i.e. for example an EC50 value in the HeLa S3 cytotoxicity test of less than 5 µmol/L, generally less than 1 µmol/L.

Measurement of Cytotoxicity on Cultivated Human Tumour Cells

To measure cytotoxicity on cultivated human tumour cells, cells of cervical carcinoma tumour cell line HeLa S3 (obtained from American Type Culture Collection (ATCC)) are cultivated in Ham's F12 Medium (Life Technologies) and 10% foetal calf serum (Life Technologies) and harvested in the log growth phase. Then the HeLa S3 cells are placed in 96-well plates (Costar) at a density of 1000 cells per well and incubated overnight in an incubator (at 37° C. and 5% CO2), while on each plate 6 wells are filled with medium alone (3 wells as the medium control, 3 wells for incubation with reduced AlamarBlue reagent). The active substances are added to the cells in various concentrations (dissolved in DMSO; DMSO final concentration: 0.1%) (in each case as a triple measurement). After 72 hours incubation 20 µl AlamarBlue reagent (AccuMed International) are added to each well, and the cells are incubated for a further 5-7 hours. As a control, 20 µl reduced AlamarBlue reagent is added to each of 3 wells (AlamarBlue reagent, which is autoclaved for 30 min). After incubation the colour change of the AlamarBlue reagent in the individual wells is determined in a Perkin Elmer fluorescence spectrophotometer (excitation 530 nm, emission 590 nm, slits 15, integrate time 0.1). The amount of AlamarBlue reagent reacted represents the metabolic activity of the cells. The relative cell activity is calculated as a percentage of the control (HeLa S3 cells without inhibitor) and the active substance concentration which inhibits the cell activity by 50% (IC50) is derived. The values are calculated from the average of three individual measurements—with correction of the dummy value (medium control).

FACS Analysis

Propidium iodide (PI) binds stoichiometrically to double-stranded DNA, and is thus suitable for determining the proportion of cells in the G1, S, and G2/M phase of the cell cycle on the basis of the cellular DNA content. Cells in the G0 and G1 phase have a diploid DNA content (2N), whereas cells in the G2 or mitosis phase have a 4N DNA content.

For PI staining, for example, $1 \times 10^6$ HeLa S3 cells are seeded onto a 75 cm2 cell culture flask, and after 24 h either 0.1% DMSO is added as control or the substance is added in various concentrations (in 0.1% DMSO). The cells are incubated for 24 h with the substance or with DMSO before the cells are washed 2× with PBS and then detached with trypsin/EDTA. The cells are centrifuged (1000 rpm, 5 min, 4° C.), and the cell pellet is washed 2× with PBS before the cells are resuspended in 0.1 ml PBS. Then the cells are fixed with 80% ethanol for 16 hours at 4° C. or alternatively for 2 hours at −20° C. The fixed cells are centrifuged (1000 rpm, 5 min, 4° C.), washed with PBS and then centrifuged again. The cell pellet is resuspended in 2 ml 0.25% Triton X-100 in PBS, and incubated on ice for 5 min before 5 ml PBS are added and the mixture is centrifuged again. The cell pellet is resuspended in 350 µl PI staining solution (0.1 mg/ml RNase A (Sigma, No. R-4875), 10 µg/ml prodium iodide (Sigma, No. P-4864) in 1× PBS). The cells are incubated for 20 min in the dark with the staining buffer before being transferred into sample measuring containers for the FACS scan. The DNA measurement is carried out in a Becton Dickinson FACS Analyzer, with an argon laser (500 mW, emission 488 nm), and the DNA Cell Quest Programme (BD). The logarithmic PI fluorescence is determined with a band-pass filter (BP 585/42). The cell populations in the individual cell cycle phases are quantified using the ModFit LT Programme made by Becton Dickinson.

The compounds according to the invention are also tested accordingly for other tumour cells.

For example, these compounds are effective on carcinomas of all kinds of tissue (e.g. breast (MCF7); colon (HCT116), head and neck (FaDu), liver (HepG2), lung (NCI-H460), stomach (NCI-N87), pancreas (BxPC-3), prostate (DU145)), sarcomas (e.g. SK-UT-1B, Saos-2), leukaemias and lymphomas (e.g. HL-60, THP-1, Raji, Jurkat, GRANTA-519) and other tumours (e.g. melanomas (BRO), gliomas (U-87MG)) and could be used for such indications. This is evidence of the broad applicability of the compounds according to the invention for the treatment of all kinds of tumour types.

The compounds of general formula (I) may be used on their own or in conjunction with other active substances according to the invention, optionally also in conjunction with other pharmacologically active substances. Suitable preparations include for example tablets, capsules, suppositories, solutions,—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

A)

| Tablets | per tablet |
|---|---|
| active substance | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

B)

| Tablets | per tablet |
|---|---|
| active substance | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

C)

| Ampoule solution | |
|---|---|
| active substance | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:
1. A compound of general formula (1)

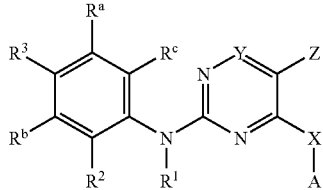
(1)

wherein
X denotes —NR$^{1a}$, O or S, and
Y denotes CH and
Z denotes halogen-C$_{1-3}$-alkyl; and
A is selected from formulae (i) or (ii)

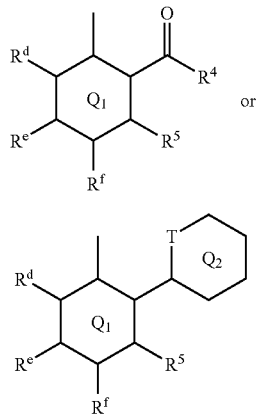

and
Q$_1$ denotes mono- or bicyclic aryl group; and
Q$_2$ denotes mono- or bicyclic heteroaryl group; and
T denotes N, O or S, and
R$^1$ and R$^{1a}$ denotes hydrogen or methyl, and
R$^2$ denotes a group selected from among —Cl, —Br, —I, —OR$^6$, —C(=O)R$^6$, —C(=O)NR$^6$R$^7$, —NR$^6$R$^7$, —NR$^6$C(=O)R$^7$, —NR$^6$SO$_2$R$^7$, —N=CR$^6$R$^7$, —SR$^6$, —SOR$^6$, —SO$_2$R$^6$, —SO$_2$NR$^6$R$^7$ and pseudohalogen, or an optionally mono- or polysubstituted group selected from among C$_{1-6}$-alkyl, C$_{2-6}$-alkenyl, C$_{2-6}$-alkynyl, C$_{3-6}$-cycloalkyl, aryl, heterocyclyl and heteroaryl, while the substituent(s) may be identical or different and are selected from among halogen, —NO$_2$, —OR$^6$, —C(=O)R$^6$, —C(=O)OR$^6$, —C(=O)NR$^6$R$^7$, —NR$^6$R$^7$, —NR$^6$C(=O)R$^7$, —NR$^6$C(=O)OR$^7$, —NR$^6$C(=O)NR$^7$R$^8$, —NR$^6$SO$_2$R$^7$, —N=CR$^6$R$^7$, —SR$^6$, —SOR$^6$, —SO$_2$R$^6$, —SO$_2$NR$^6$R$^7$, —NR$^6$SO$_2$NR$^7$R$^8$, —OSO$_2$NR$^7$R$^8$ and pseudohalogen; and R$^a$, R$^b$, R$^c$, R$^d$, R$^e$ and R$^f$ each independently of one another denote a group selected from among hydrogen, halogen, —NO$_2$, —OR$^6$, —C(=O)R$^6$, —C(=O)OR$^6$, —C(=O)NR$^6$R$^7$, —NR$^6$R$^7$, —NR$^6$C(=O)R$^7$, —NR$^6$C(=O)OR$^7$, —NR$^6$C(=O)NR$^7$R$^8$, —NR$^6$SO$_2$R$^7$, —N=CR$^6$R$^7$, —SR$^6$, —SOR$^6$, —SO$_2$R$^6$, —SO$_2$NR$^6$R$^7$, —NR$^6$SO$_2$NR$^7$R$^8$, —OSO$_2$NR$^7$R$^8$ and pseudohalogen;

or an optionally mono- or polysubstituted group selected from among C$_{1-6}$-alkyl, C$_{2-6}$-alkenyl, C$_{2-6}$-alkynyl, C$_{3-6}$-cycloalkyl, aryl, heterocyclyl and heteroaryl, while the substituent(s) may be identical or different and are selected from among hydrogen, halogen, —NO$_2$, —OR$^6$, —C(=O)R$^6$, —C(=O)OR$^6$, —C(=O)NR$^6$R$^7$, —NR$^6$R$^7$, —NR$^6$C(=O)R$^7$, —NR$^6$C(=O)OR$^7$, —NR$^6$C(=O)NR$^7$R$^8$, —NR$^6$SO$_2$R$^7$, —N=CR$^6$R$^7$, —SR$^6$, —SOR$^6$, —SO$_2$R$^6$, —SO$_2$NR$^6$R$^7$, —NR$^6$SO$_2$NR$^7$R$^8$, —OSO$_2$NR$^7$R$^8$ and pseudohalogen; and R$^3$ is selected from the formulae (iii)-(ix),

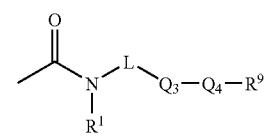
(iii)

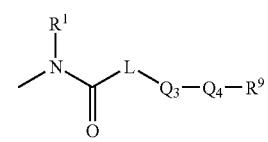
(iv)

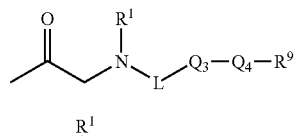
(v)

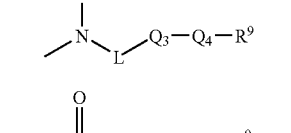
(vi)

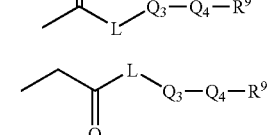
(vii)

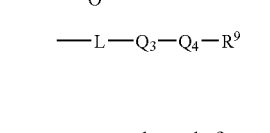
(viii)

—L—Q$_3$—Q$_4$—R$^9$
(ix)

and
R$^4$ denotes a group selected from among hydrogen, —OR$^6$, —C(=O)R$^6$, —C(=O)OR$^6$, —C(=O)NR$^6$R$^7$, —NR$^6$R$^7$, —NR$^6$C(=O)R$^7$, —NR$^6$C(=O)OR$^7$, —NR$^6$C(=O)NR$^7$R$^8$, —NR$^6$SO$_2$R$^7$, —N=CR$^6$R$^7$, —SR$^6$, —SOR$^6$, —SO$_2$R$^6$, —SO$_2$NR$^6$R$^7$, —NR$^6$SO$_2$NR$^7$R$^8$, —OSO$_2$NR$^7$R$^8$ and pseudohalogen, or denotes a group selected from among optionally mono- or polysubstituted C$_{1-8}$-alkyl, C$_{2-10}$-alkenyl, C$_{2-10}$-alkynyl, C$_{3-8}$-cycloalkyl, aryl, heterocyclyl and heteroaryl, while the substituent(s) may be identical or different and are selected from among C$_{1-8}$-alkyl, halogen, —NO$_2$, —OR$^6$, —C(=O)R$^6$, —C(=O)OR$^6$, —C(=O)NR$^6$R$^7$, —NR$^6$R$^7$, —NR$^6$C(=O)R$^7$, —NR$^6$C(=O)OR$^7$, —NR$^6$C(=O)NR$^7$R$^8$, —NR$^6$SO$_2$R$^7$, —N=CR$^6$R$^7$, —SR$^6$, —SOR$^6$, —SO$_2$R$^6$, —SO$_2$NR$^6$R$^7$, —NR$^6$SO$_2$NR$^7$R$^8$, —OSO$_2$NR$^7$R$^8$ and pseudohalogen; and R$^5$ denotes hydrogen, halogen, —CF$_3$, C$_{1-3}$-alkyl or —OR$^6$; and $R^6$, $R^7$ and $R^8$ in each case independently of one another denote hydrogen or a group selected from among optionally mono- or polysubstituted $C_{1-5}$-alkyl, $C_{2-5}$-alkenyl, $C_{2-5}$-alkynyl, $C_{3-10}$-cycloalkyl, aryl, heterocyclyl and heteroaryl, while the substituent(s) may be identical or different and are selected from among $C_{3-10}$-cycloalkyl, aryl, heterocyclyl, heteroaryl, halogen, —$NO_2$, —$OR^{10}$, —$C(=O)R^{10}$, —$C(=O)OR^{10}$, —$C(=O)NR^{10}R^{11}$, —$NR^{10}R^{11}$, —$NR^{10}C(=O)R^{11}$, —$NR^{10}C(=O)OR^{11}$, —$NR^{10}C(=O)NR^{11}R^{12}$, —$NR^{10}C(=O)ONR^{11}R^{12}$, —$NR^{10}SO_2R^{11}$, —$N=CR^{10}R^{11}$, —$SR^{10}$, —$SOR^{10}$, —$SO_2R^{10}$, —$SO_2NR^{10}R^{11}$, —$NR^{10}SO_2NR^{11}R^{12}$, —$OSO_2NR^{10}R^{11}$ und pseudohalogen; and L denotes a bond or a group selected from among optionally mono- or polysubstituted $C_{1-16}$-alkyl, $C_{2-16}$-alkenyl, $C_{2-16}$-alkynyl, $C_{3-10}$-cycloalkyl, aryl, heterocyclyl and heteroaryl, while the substituent(s) may be identical or different and are selected from among halogen, —$NO_2$, —$OR^{10}$, —$C(=O)R^{10}$, —$C(=O)OR^{10}$, —$C(=O)NR^{10}R^{11}$, —$NR^{10}R^{11}$, —$NR^{10}COR^{11}$, —$NR^{10}C(=O)OR^{11}$, —$NR^{10}C(=O)NR^{10}R^{11}$, —$NR^{10}C(=O)ONR^{11}R^{12}$, —$NR^{10}SO_2R^{11}$, —$N=CR^{10}R^{11}$, —$SR^{10}$, —$SOR^{10}$, —$SO_2R^{10}$, —$SO_2NR^{10}R^{11}$, —$NR^{10}SO_2NR^{11}R^{12}$, —$OSO_2NR^{10}R^{11}$ and pseudohalogen; and $Q_3$ and $Q_4$ independently of one another denote a bond or a group selected from among optionally mono- or polysubstituted mono- or bicyclic heterocyclyl while the substituent(s) may be identical or different and are selected from among methyl, ethyl, halogen, —$NH_2$, —OH and pseudohalogen; and $R^9$ denotes a group selected from among optionally mono- or polysubstituted $C_{1-16}$-alkyl, $C_{2-16}$-alkenyl, $C_{2-16}$-alkynyl, $C_{3-10}$-cycloalkyl, aryl, heterocyclyl and heteroaryl, while the substituent(s) may be identical or different and are selected from among halogen, —$NO_2$, —$OR^{10}$, —$C(=O)R^{10}$, —$C(=O)OR^{10}$, —$C(=O)NR^{10}R^{11}$, —$NR^{10}R^{11}$, —$NR^{10}COR^{11}$, —$NR^{10}C(=O)OR^{11}$, —$NR^{10}C(=O)NR^{11}R^{12}$, —$NR^{10}C(=O)ONR^{11}R^{12}$, —$NR^{10}SO_2R^{11}$, —$N=CR^{10}R^{11}$, —$SR^{10}$, —$SOR^{10}$, —$SO_2R^{10}$, —$SO_2NR^{10}R^{11}$, —$NR^{10}SO_2NR^{11}R^{12}$, —$OSO_2NR^{10}R^{11}$ and pseudohalogen; and $R^{10}$, $R^{11}$ and $R^{12}$ in each case independently of one another denote hydrogen or a group selected from among optionally mono- or polysubstituted $C_{1-8}$-alkyl, $C_{2-8}$-alkenyl, $C_{2-8}$-alkynyl, $C_{3-10}$-cycloalkyl, aryl, heterocyclyl and heteroaryl, while the substituent(s) may be identical or different and are selected from among halogen, —$NH_2$, —OH and pseudohalogen;

optionally in the form of a tautomer, racemate, enantiomer, diastereomer, or a mixture thereof, or a pharmacologically acceptable acid addition salt thereof.

2. The compound of general formula (1), according to claim 1, wherein

X denotes —$NR^{1a}$ or oxygen, and

A is selected from formulae (i) or (ii)

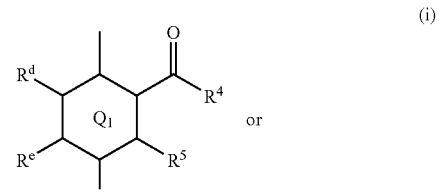

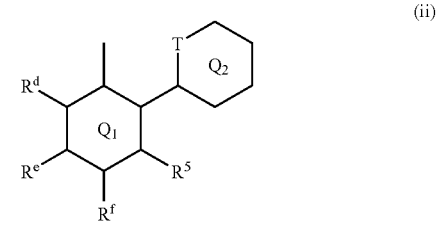

and $Q_1$ denotes mono- or bicyclic aryl group; and
$Q_2$ denotes monocyclic heteroaryl group; and
T denotes N, O or S, and
$R^1$ and $R^{1a}$ denotes hydrogen; and
$R^3$ denotes formula (iii),

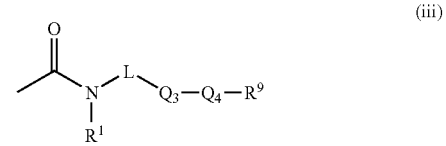

and the other groups are as defined in claim 1.

3. The compound of general formula (1), according to claim 1, wherein

Y denotes CH; and
$Q_1$ denotes monocyclic aryl group and the other groups are as defined in claim 1.

4. The compound of general formula (1), according to claim 1, wherein $R^c$ denotes a group selected from among hydrogen, —F, —Cl, methyl and ethyl and the other groups are as defined in claim 1.

5. The compound of general formula (1), according to claim 1, wherein $R^a$ and $R^b$ in each case independently of one another denote hydrogen or an optionally mono- or polysubstituted group selected from among $C_{1-2}$-alkyl, $C_2$-alkenyl, $C_2$-alkynyl, $C_{3-6}$-cycloalkyl, aryl, heterocyclyl and heteroaryl, wherein the substituent(s) may be identical or different and are selected from among hydrogen, halogen, —$NO_2$, —$OR^6$, —$C(=O)R^6$, —$C(=O)OR^6$, —$C(=O)NR^6R^7$, —$NR^6R^7$, —$NR^6C(=O)R^7$, —$NR^6C(=O)OR^7$, —$NR^6C(=O)NR^7R^8$, —$NR^6SO_2R^7$, —$N=CR^6R^7$, —$SR^6$, —$SOR^6$, —$SO_2R^6$, —$SO_2NR^6R^7$, —$NR^6$, —$SO_2NR^7R^8$, —$OSO_2NR^7R^8$ and pseudohalogen and the other groups are as defined in claim 1.

6. The compound of general formula (1), according to claim 1, wherein $R^a$ and $R^b$ denotes hydrogen and the other groups are as defined in claim 1.

7. The compound of general formula (1), according to claim 1, wherein
Z denotes $C_{1-3}$-fluoroalkyl and
Y denotes CH
and the other groups are as defined in claim 1.

8. A pharmaceutical composition comprising the compound of general formula (1), according to claim 1 or a pharmaceutically active salt thereof.

9. A pharmaceutical composition comprising as active substances one or more compounds of general formula (I) according to claim 1, or a physiologically acceptable salt thereof, and one or more conventional excipients and/or carriers.

10. A method for the treatment of prostate cancer in a patient comprising administering to said patient a therapeutically effective amount of a compound according to claim 1 or a pharmaceutical composition according to claim 9 or a pharmaceutical composition according to claim 9.

11. A pharmaceutical composition comprising a compound of general formula (1)

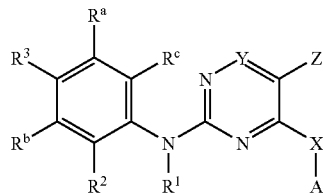
(1)

wherein
X denotes —NR$^{1a}$, O or S, and
Y denotes CH and
Z denotes halogen-$C_{1-3}$-alkyl; and
A is selected from formulae (i) or (ii)

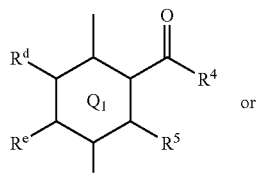
(i)

or

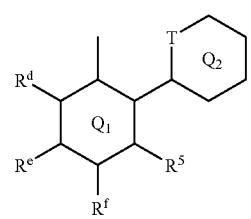
(ii)

and
$Q_1$ denotes mono- or bicyclic aryl group; and
$Q_2$ denotes mono- or bicyclic heteroaryl group; and
T denotes N, O or S, and
$R^1$ and $R^{1a}$ denote hydrogen or methyl, and
$R^2$ denotes a group selected from among —Cl, —Br, —I, —OR$^6$, —C(=O)R$^6$, —C(=O)NR$^6$R$^7$, —NR$^6$R$^7$, —NR$^6$C(=O)R$^7$, —NR$^6$SO$_2$R$^7$, —N=CR$^6$R$^7$, —SR$^6$, —SOR$^6$, —SO$_2$R$^6$, —SO$_2$NR$^6$R$^7$ and pseudohalogen, or an optionally mono- or polysubstituted group selected from among $C_{1-6}$-alkyl, $C_{2-6}$-alkenyl, $C_{2-6}$-alkynyl, $C_{3-6}$-cycloalkyl, aryl, heterocyclyl and heteroaryl, wherein the substituent(s) may be identical or different and are selected from among halogen, —NO$_2$, —OR$^6$, —C(=O)R$^6$, —C(=O)OR$^6$, —C(=O)NR$^6$R$^7$, —NR$^6$R$^7$, —NR$^6$C(=O)R$^7$, —NR$^6$C(=O)OR$^7$, —NR$^6$C(=O)NR$^7$R$^8$, —NR$^6$SO$_2$R$^7$, —N=CR$^6$R$^7$, —SR$^6$, —SOR$^6$, —SO$_2$R$^6$, —SO$_2$NR$^6$R$^7$, —NR$^6$SO$_2$NR$^7$R$^8$, —OSO$_2$NR$^7$R$^8$ and pseudohalogen; and $R^a$, $R^b$, $R^c$, $R^d$, $R^e$ and $R^f$ each independently of one another denote a group selected from among hydrogen, halogen, —NO$_2$, —OR$^6$, —C(=O)R$^6$, —C(=O)OR$^6$, —C(=O)NR$^6$R$^7$, —NR$^6$R$^7$, —NR$^6$C(=O)R$^7$, —NR$^6$C(=O)OR$^7$, —NR$^6$C(=O)NR$^7$R$^8$, —NR$^6$SO$_2$R$^7$, —N=CR$^6$R$^7$, —SR$^6$, —SOR$^6$, —SO$_2$R$^6$, —SO$_2$NR$^6$R$^7$, —NR$^6$SO$_2$NR$^7$R$^8$, —OSO$_2$NR$^7$R$^8$ and pseudohalogen;

or an optionally mono- or polysubstituted group selected from among $C_{1-6}$-alkyl, $C_{2-6}$-alkenyl, $C_{2-6}$-alkynyl, $C_{3-6}$-cycloalkyl, aryl, heterocyclyl and heteroaryl, wherein the substituent(s) may be identical or different and are selected from among hydrogen, halogen, —NO$_2$, —OR$^6$, —C(=O)R$^6$, —C(=O)OR$^6$, —C(=O)NR$^6$R$^7$, —NR$^6$R$^7$, —NR$^6$C(=O)R$^7$, —NR$^6$C(=O)OR$^7$, —NR$^6$C(=O)NR$^7$R$^8$, —NR$^6$SO$_2$R$^7$, —N=CR$^6$R$^7$, —SR$^6$, —SOR$^6$, —SO$_2$R$^6$, —SO$_2$NR$^6$R$^7$, —NR$^6$SO$_2$NR$^7$R$^8$, —OSO$_2$NR$^7$R$^8$ and pseudohalogen; and $R^3$ is selected from the formulae (iii)-(ix),

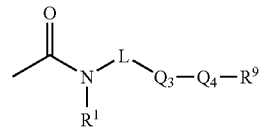
(iii)

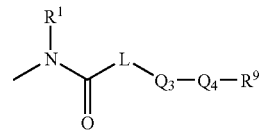
(iv)

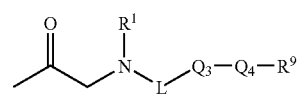
(v)

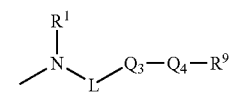
(vi)

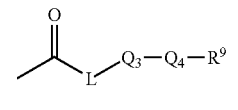
(vii)

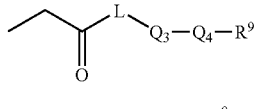
(viii)

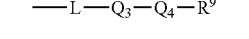
(ix)

and
$R^4$ denotes a group selected from among hydrogen, —OR$^6$, —C(=O)R$^6$, —C(=O)OR$^6$, —C(=O)NR$^6$R$^7$, —NR$^6$R$^7$, —NR$^6$C(=O)R$^7$, —NR$^6$C(=O)

$OR^7$, —$NR^6C(=O)NR^7R^8$, —$NR^6SO_2R^7$, —$N=CR^6R^7$, —$SR^6$, —$SOR^6$, —$SO_2R^6$, —$SO_2NR^6R^7$, —$NR^6SO_2NR^7R^8$, —$OSO_2NR^7R^8$ and pseudohalogen, or denotes a group selected from among optionally mono- or polysubstituted $C_{1-8}$-alkyl, $C_{2-10}$-alkenyl, $C_{2-10}$-alkynyl, $C_{3-8}$-cycloalkyl, aryl, heterocyclyl and heteroaryl, wherein the substituent(s) may be identical or different and are selected from among $C_{1-8}$-alkyl, halogen, —$NO_2$, —$OR^6$, —$C(=O)R^6$, —$C(=O)OR^6$, —$C(=O)NR^6R^7$, —$NR^6R^7$, —$NR^6C(=O)R^7$, —$NR^6C(=O)OR^7$, —$NR^6C(=O)NR^7R^8$, —$NR^6SO_2R^7$, —$N=CR^6R^7$, —$SR^6$, —$SOR^6$, —$SO_2R^6$, —$SO_2NR^6R^7$, —$NR^6SO_2NR^7R^8$, —$OSO_2NR^7R^8$ and pseudohalogen; and $R^5$ denotes hydrogen, halogen, —$CF_3$, $C_{1-3}$-alkyl or —$OR^6$; and $R^6$, $R^7$ and $R^8$ in each case independently of one another denote hydrogen or a group selected from among optionally mono- or polysubstituted $C_{1-5}$-alkyl, $C_{2-5}$-alkenyl, $C_{2-5}$-alkynyl, $C_{3-10}$-cycloalkyl, aryl, heterocyclyl and heteroaryl, wherein the substituent(s) may be identical or different and are selected from among $C_{3-10}$-cycloalkyl, aryl, heterocyclyl, heteroaryl, halogen, —$NO_2$, —$OR^{10}$, —$C(=O)R^{10}$, —$C(=O)OR^{10}$, —$C(=O)NR^{10}R^{11}$, —$NR^{10}R^{11}$, —$NR^{10}C(=O)R^{11}$, —$NR^{10}C(=O)OR^{11}$, —$NR^{10}C(=O)NR^{11}R^{12}$, —$NR^{10}C(=O)ONR^{11}R^{12}$, —$NR^{10}SO_2R^{11}$, —$N=CR^{10}R^{11}$, —$SR^{10}$, —$SOR^{10}$, —$SO_2R^{10}$, —$SO_2NR^{10}R^{11}$, —$NR^{10}SO_2NR^{11}R^{12}$, —$OSO_2NR^{10}R^{11}$ und pseudohalogen; and L denotes a bond or a group selected from among optionally mono- or polysubstituted $C_{1-16}$-alkyl, $C_{2-16}$-alkenyl, $C_{2-16}$-alkynyl, $C_{3-10}$-cycloalkyl, aryl, heterocyclyl and heteroaryl, wherein the substituent(s) may be identical or different and are selected from among halogen, —$NO_2$, —$OR^{10}$, —$C(=O)R^{10}$, —$C(=O)OR^{10}$, —$C(=O)NR^{10}R^{11}$, —$NR^{10}R^{11}$, —$NR^{10}COR^{11}$, —$NR^{10}C(=O)OR^{11}$, —$NR^{10}C(=O)NR_{11}R^{12}$, —$NR^{10}C(=O)ONR^{11}R^{12}$, —$NR^{10}SO_2R^{11}$, —$N=CR^{10}R^{11}$, —$SR^{10}$, —$SOR^{10}$, —$SO_2R^{10}$, —$SO_2NR^{10}R^{11}$, —$NR^{10}SO_2NR^{11}R^{12}$, —$OSO_2NR^{10}R^{11}$ and pseudohalogen; and $Q_3$ and $Q_4$ independently of one another denote a bond or a group selected from among optionally mono- or polysubstituted mono- or bicyclic heterocyclyl while the substituent(s) may be identical or different and are selected from among methyl, ethyl, halogen, —$NH_2$, —$OH$ and pseudohalogen; and $R^9$ denotes a group selected from among optionally mono- or polysubstituted $C_{1-16}$-alkyl, $C_{2-16}$-alkenyl, $C_{2-16}$-alkynyl, $C_{3-10}$-cycloalkyl, aryl, heterocyclyl and heteroaryl, wherein the substituent(s) may be identical or different and are selected from among halogen, —$NO_2$, —$OR^{10}$, —$C(=O)R^{10}$, —$C(=O)OR^{10}$, —$C(=O)NR^{10}R^{11}$, —$NR^{10}R^{11}$, —$NR^{10}COR^{11}$, —$NR^{10}C(=O)OR^{11}$, —$NR^{10}C(=O)NR^{11}R^{12}$, —$NR^{10}C(=O)ONR^{11}R^{12}$, —$NR^{10}SO_2R^{11}$, —$N=CR^{10}R^{11}$, —$SR^{10}$, —$SOR^{10}$, —$SO_2R^{10}$, —$SO_2NR^{10}R^{11}$, —$NR^{10}SO_2NR^{11}R^{12}$, —$OSO_2NR^{10}R^{11}$ and pseudohalogen; and $R^{10}$, $R^{11}$ and $R^{12}$ in each case independently of one another denote hydrogen or a group selected from among optionally mono- or polysubstituted $C_{1-8}$-alkyl, $C_{2-8}$-alkenyl, $C_{2-8}$-alkynyl, $C_{3-10}$-cycloalkyl, aryl, heterocyclyl and heteroaryl, wherein the substituent(s) may be identical or different and are selected from among halogen, —$NH_2$, —$OH$ and pseudohalogen;

optionally in the form of a tautomer, racemate, enantiomer, diastereomer, or a mixture thereof, or a pharmacologically acceptable acid addition salt thereof, and at least one other active substance selected from among cytostatic active substances, cytotoxic active substances, steroids and antibodies, optionally in the form of a tautomer, racemate, enantiomer, diastereomer, or a mixtures thereof, or a pharmacologically acceptable acid addition salt thereof.

12. The compound of general formula (1) according to claim 1, wherein

Z denotes $CF_3$.

13. The compound of general formula (1) according to claim 7, wherein

Z denotes $CF_3$.

* * * * *